US010294460B2

(12) United States Patent
Segers et al.

(10) Patent No.: US 10,294,460 B2
(45) Date of Patent: May 21, 2019

(54) PROCESS FOR THE PURIFICATION OF POLIOVIRUS FROM CELL CULTURES

(71) Applicant: Janssen Vaccines & Prevention B.V., Leiden (NL)

(72) Inventors: Mariken Segers, Leiden (NL); Beckley Kungah Nfor, Leiden (NL); Feras Nachmi Alazi, Leiden (NL); Marcel Leo De Vocht, Leiden (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 0 days.

(21) Appl. No.: 15/325,650

(22) PCT Filed: Jul. 21, 2015

(86) PCT No.: PCT/EP2015/066638
§ 371 (c)(1),
(2) Date: Jan. 11, 2017

(87) PCT Pub. No.: WO2016/012445
PCT Pub. Date: Jan. 28, 2016

(65) Prior Publication Data

US 2017/0166872 A1 Jun. 15, 2017

(30) Foreign Application Priority Data

Jul. 24, 2014 (EP) .................................... 14178392
Jul. 24, 2014 (EP) .................................... 14178399

(51) Int. Cl.
*C12N 7/00* (2006.01)

(52) U.S. Cl.
CPC ...... *C12N 7/00* (2013.01); *C12N 2770/32611* (2013.01); *C12N 2770/32651* (2013.01)

(58) Field of Classification Search
None
See application file for complete search history.

(56) References Cited

U.S. PATENT DOCUMENTS

| | | | | |
|---|---|---|---|---|
| 4,525,349 | A | 6/1985 | Montagnon et al. | |
| 5,994,128 | A | 11/1999 | Fallaux et al. | |
| 6,903,191 | B2 | 6/2005 | de Vocht et al. | |
| 7,326,555 | B2 | 2/2008 | Konz, Jr. et al. | |
| 8,460,920 | B2 | 6/2013 | De Vocht et al. | |
| 8,470,585 | B2 | 6/2013 | De Vocht et al. | |
| 2012/0202267 | A1* | 8/2012 | De Vocht ................ | C12N 7/00 435/239 |
| 2013/0330716 | A1* | 12/2013 | Dorange .......... | G01N 33/56983 435/5 |

FOREIGN PATENT DOCUMENTS

| | | | |
|---|---|---|---|
| JP | 2004-313019 | A | 11/2004 |
| JP | 2004313019 | A | 11/2004 |
| JP | 2007-295937 | A | 11/2007 |
| JP | 2012-532616 | A | 12/2012 |
| JP | 2014-516554 | A | 7/2014 |
| WO | 02/074940 | A1 | 9/2002 |
| WO | 02074940 | A1 | 9/2002 |
| WO | 2004099396 | A1 | 11/2004 |
| WO | 2005095578 | A1 | 10/2005 |
| WO | 2006042414 | A1 | 4/2006 |
| WO | 2007007344 | A1 | 1/2007 |
| WO | 2008006494 | A1 | 1/2008 |
| WO | 2011/006823 | A1 | 1/2011 |
| WO | 2011006823 | A1 | 1/2011 |
| WO | 2011045378 | A1 | 4/2011 |
| WO | 2011045381 | A1 | 4/2011 |
| WO | 2012/168003 | A1 | 12/2012 |
| WO | 2012168003 | A1 | 12/2012 |
| WO | 2016012445 | A2 | 1/2016 |

OTHER PUBLICATIONS

Fuchs et al., Establishment of European Pharmacopoeia BRP batch 2 for inactivated poliomyelitis vaccine for in vitro D-antigen assay. Pharmeuropa Bio. Jan. 2003, pp. 23-50, 2003.
WHO Technical Reports Series, No. 910, 2002, Recommendations for the production and control of poliomyelitis vaccine (inactivated).
Kreeftenberg et al., Technology transfer of Sabin-IPV to new developing country markets, Biologicals, 2006; 34 (2):155-8.
Bakker et al., Inactivated polio vaccine development for technology transfer using attenuated Sabin poliovirus strains to shift from Salk-IPV to Sabin-IPV, Vaccine, 2011; 29(41):7188-96.
Westdijk et al., Characterization and standardization of Sabin-based inactivated polio vaccine: Proposal for a new antigen unit for inactivated polio vaccines, Vaccine, 2011; 29:3390-3397.
Sanders et al., PER.C6® cells as a serum-free suspension cell platform for the production of high titer poliovirus: a potential low cost of goods option for world supply of inactivated poliovirus vaccine, Vaccine, 2013; 31(5):850-6.
Thomassen et al., Isoelectric focusing with whole column imaging detection, Anal. Chem., 85:6089-6094 (2013).
Thomassen et al., Scale down of the inactivated polio production process, Biotechnology and Bioengineering, vol. 110 (5):1354-1365, May 2013.
Vlecken et al., Comparison of initial feasibility of host cell lines for viral vaccine production, Journal of Virological Methods, 2013, 193 (2):278-283.
Merten et al., 1997, Evaluation of the serum-free medium MDSS2 for the production of poliovirus on Vero cells in bioreactors.
Henderson et al., Concentration and purification of enteroviruses by membrane chromatography, Applied and Environmental Microbiology, Nov. 1976, p. 689-693.
Cortin et al., High-Titer Poliovirus Vector Production in 293S Cell Perfusion Culture, Biotechnol. Prog. 2004, European Pharmacopoeia 7.0, Poliomyelitis vaccine (inactivated). Apr. 2010:0214.
Yuk et al., Perfusion Cultures of Human Tumor Cells: A Scalable Production Platform for Oncolytic Adenoviral Vectors, Biotechnol. Bioengin. 86:637-641 (2004).

(Continued)

*Primary Examiner* — Benjamin P Blumel
(74) *Attorney, Agent, or Firm* — Kramer Amado, P.C.

(57) ABSTRACT

The disclosure provides methods for poliovirus purification from crude cell culture harvests using a detergent followed by a clarification step.

11 Claims, 8 Drawing Sheets

(56) References Cited

OTHER PUBLICATIONS

Goerke et al., Development of a Novel Poliovirus Purification Process Utilizing Selective Precipitation of Cellular DNA, Biotechnology and Bioengineering, vol. 91, No. 1, Jul. 5, 2005.
PCT International Written Opinion, PCT/EP2015/066638, dated Feb. 2, 2016.
PCT International Search Report, PCT/EP2015/066638, dated Feb. 2, 2016.

* cited by examiner

A
B
C

A

B

PROCESS FOR THE PURIFICATION OF POLIOVIRUS FROM CELL CULTURES

CROSS-REFERENCE TO RELATED APPLICATIONS

This application is a national phase entry under 35 U.S.C. § 371 of International Patent Application PCT/EP2015/066638, filed Jul. 21, 2015, designating the United States of America and published in English as International Patent Publication WO 2016/012445 A2 on Jan. 28, 2016, which claims the benefit under Article 8 of the Patent Cooperation Treaty to European Patent Application Serial Nos. 14178399.3 and 14178392.8, both filed Jul. 24, 2014.

TECHNICAL FIELD

The application relates to the field of biotechnology and virus production. More particularly, it concerns improved methods for the purification of poliovirus particles from a cell suspension.

BACKGROUND

Recent developments in the field of vaccine production have created the need for large-scale manufacturing. Robust and high-yield processes are needed to support the world with sufficient amounts of (recombinant) vaccines to combat infectious diseases such as Polio.

Polioviruses are members of the *Enterovirus* genus of the family Picornaviridae. Polioviruses are small, non-enveloped viruses with capsids enclosing a single-stranded, positive sense RNA genome. There are three types of polioviruses: types 1, 2 and 3. Infections of susceptible individuals by poliovirus can result in paralytic poliomyelitis. Poliomyelitis is highly contagious. Two different polio vaccines have been developed over time, the inactivated poliovirus vaccine (IPV) of Salk and the live attenuated oral poliovirus vaccine (OPV) of Sabin. Both vaccines are safe and effective. Each has its particular advantages and disadvantages, and both have played an important role in the control of poliomyelitis. For a review about polioviruses and polio vaccines, see, e.g., Kew et al., 2005.

The culture and purification systems for producing bulk poliovirus material that can be used in a vaccine, in particular, for IPV, contribute to a large extent to the relatively high costs.

Thus, there remains a need in the art for efficient culture and purification systems for producing poliovirus for use in vaccines; in particular, there remains a need for purification processes for polioviruses with high yields.

In a typical poliovirus production process, cells are grown in specific medium and poliovirus is subsequently placed in contact with the cells to allow the virus to infect the cells and to propagate. After propagation of the poliovirus in the cells, the virus or components thereof are harvested from the cell culture.

One preferred currently used IPV manufacturing process uses anchorage-dependent, monkey-derived VERO cells that are grown on microcarriers and cultured in serum-supplemented media.

The virus produced and released in the cell culture medium can be separated from the cellular biomass by conventional methods, such as depth filtration and centrifugation. In such a case, the filtration or centrifugation is the harvesting step. The filtered harvest is typically ultra-filtrated to concentrate the viral suspension and, subsequently, the poliovirus can be purified, e.g., using gel filtration and/or ion exchange chromatography. Methods for harvesting and purifying poliovirus or viral components, and production of vaccines therefrom, have been used in the art for decades already, and thus are well known and have been amply described, for example, in Van Wezel et al., 1978; Montagnon et al., 1984; WO 2007/007344 and U.S. Pat. No. 4,525,349, all incorporated by reference herein. The resulting concentrated virus suspension can optionally be diluted, and for preparing IPV, the poliovirus therein will be inactivated, for which conventional methods can be used.

The productivities of the currently used poliovirus production processes are not sufficient to gear up IPV production volumes needed for eradicating Polio on a worldwide scale. Hence, there is a limitation in the global production capacity. In addition, the currently used production processes, due to their low productivity, have high unit operation costs because of large facility footprint and correspondingly high medium and buffer consumption, together with high (bioactive) waste production. Apart from costs associated with the vaccine manufacturing process, also product batch control and release costs scale with productivity, i.e., high productivity batches significantly drive down costs per vaccine dose.

One way of improving the yields of poliovirus production is to improve the upstream production process. Processes for production of poliovirus at high yields have been achieved by increasing the cell density of the production cultures (see, e.g., WO 2011/06823), which, however, may pose additional challenges in downstream processing. No developments for improving poliovirus purification processes have been described hitherto, either for lower or high-density cultures.

Therefore, there is a need in the industry for improved downstream processes to further increase the yields of purification processes for poliovirus.

BRIEF SUMMARY

This disclosure relates to improved methods of purifying poliovirus particles from a crude cell harvest, and is also suitable for harvests with high cell density. In certain exemplary embodiments, the methods of this disclosure may, for instance, have overall productivity ranging between 15-25, 6-12 and 10-16 dose IPV/ml virus culture, post-formaldehyde inactivation for poliovirus types 1, 2 and 3, respectively. This is a substantially higher volumetric yield than the methods known hitherto. Indeed, Kreeftenberg et al. (2006) have estimated the overall yields for conventional, VERO cell platform-based, IPV processes to be 0.64, 1.04 and 0.34 dose/ml virus culture, based on a 40:8:32 D-antigen Units/dose for poliovirus types 1-3, respectively, and assuming an overall D-antigen recovery after inactivation of 40%. The noted significant increase in productivity will translate to eminent reduction of facility footprint with consequent lowering of manufacturing costs, while providing maximum capacity needed to supply the global demand for IPV doses.

Downstream processing of high cell density suspensions using known processes would commonly require a multitude of steps. A first filtration step would consist of a course filtration to remove whole cells, succeeded with a series of smaller size membrane filters to remove residual cell debris and precipitate material. Subsequently, after a concentration step, two or more selective chromatography steps are required to obtain a sufficiently purified poliovirus suspension according to regulatory requirements (WHO/EP).

It has been found and disclosed herein that directly after propagating poliovirus in a cell culture, the obtained crude cell culture harvest containing poliovirus could be treated with a detergent, preferably selected from the group of cationic detergent, anionic detergent, non-ionic detergent and zwitterionic detergent in order to improve the release of poliovirus into the harvest suspension. The so-obtained overall purification yields were unprecedented. Indeed, in certain embodiments, the process of this disclosure reached yields of 6-25 IPV dose/ml cell suspension as opposed to conventional Vero cell-based platforms yields of 0.3-1 IPV doses/ml cell suspension, obtained using processes as disclosed hitherto.

The disclosure provides a method of purifying poliovirus from a crude cell culture harvest, the method comprising the steps of: a) adding a detergent to the crude cell culture harvest; and b) clarifying the poliovirus-containing cell culture harvest to obtain a clarified harvest with poliovirus particles.

The disclosure also provides a method of enhancing poliovirus release from a crude cell culture harvest, the method comprising the steps of: a) adding a detergent to the crude cell culture harvest; and b) clarifying the poliovirus-containing cell culture harvest to obtain a clarified harvest with poliovirus particles.

The clarification step results in a clarified harvest, which comprises a content strongly reduced in host cell DNA and cell debris, as compared to the crude cell culture harvest.

Surprisingly, post clarification, a highly selective cationic exchange capture step followed by a size separation-based polish step, i.e., size exclusion chromatography or diafiltration process step, was able to accommodate for removal of high levels of Host Cell Protein (HCP) impurities from clarified harvests.

Therefore, this disclosure also provides a method of purifying poliovirus from a cell culture, the method comprising the steps of: a) adding a detergent to the cell culture; b) clarifying the poliovirus-containing cell culture to obtain a clarified harvest with poliovirus particles; and c) subjecting the clarified harvest obtained in step b) to a capture step to obtain a poliovirus-containing suspension. Preferably, the capture step is a cationic exchange chromatography step.

In a preferred embodiment, the poliovirus obtained in step c) of the previous methods is further separated from the poliovirus-containing suspension by size exclusion. Preferably, size exclusion is performed by size-exclusion chromatography.

In a preferred embodiment, the disclosure also provides a method of purifying poliovirus from a cell culture, the method comprising the steps of: a) adding a detergent to the cell culture; b) clarifying the poliovirus-containing cell culture to obtain a clarified harvest with poliovirus particles; c) subjecting the clarified harvest obtained in step b) to a cationic exchange chromatography step to obtain a poliovirus-containing suspension; and d) further purifying the poliovirus from the poliovirus-containing suspension by size-exclusion chromatography.

The detergent used in this disclosure is preferably selected from the group of cationic detergents, anionic detergents, non-ionic detergents and zwitterionic detergents. In an even more preferred embodiment, the detergent is a cationic detergent, preferably the cationic detergent is selected from the group of Hexadecyltrimethylammonium bromide (CTAB), Hexadecylpyridinium chloride (CPC), Benzethonium chloride (BTC) and domiphen bromide (DB). In a more preferred embodiment, the detergent is domiphen bromide (DB).

In yet another embodiment, the preferred detergent is an anionic detergent.

Preferably, the anionic detergent is selected from the group of Sodium taurodeoxycholate hydrate (STH) and Sodium dodecyl sulfate (SDS).

In yet another embodiment, the preferred detergent is a non-ionic detergent. Preferably, the non-ionic detergent is selected from the group of 4-(1,1,3,3-Tetramethylbutyl)phenyl-polyethylene glycol (TRITON® X-100) and Decyl-β-D-1-thiomaltopyranoside (DTP).

In another embodiment, the preferred detergent is a zwitterionic detergent. Preferably, the zwitterionic detergent is selected from the group of 3-(N,N-Dimethylmyristylammonio) propanesulfonate (SB3-14), 3-[(3-Cholamidopropyl)dimethylammonio]-1-propanesulfonate (CHAPS).

This disclosure also provides for the use of a detergent for enhancing the release of poliovirus from a crude cell culture harvest.

BRIEF DESCRIPTION OF THE DRAWINGS

FIG. 6. (Panel B) Host cell DNA precipitation in poliovirus-containing crude cell culture harvests as a result of the treatment with different cationic detergents; CTAB, CPC and BTC, respectively.

DETAILED DESCRIPTION

Figure 1:
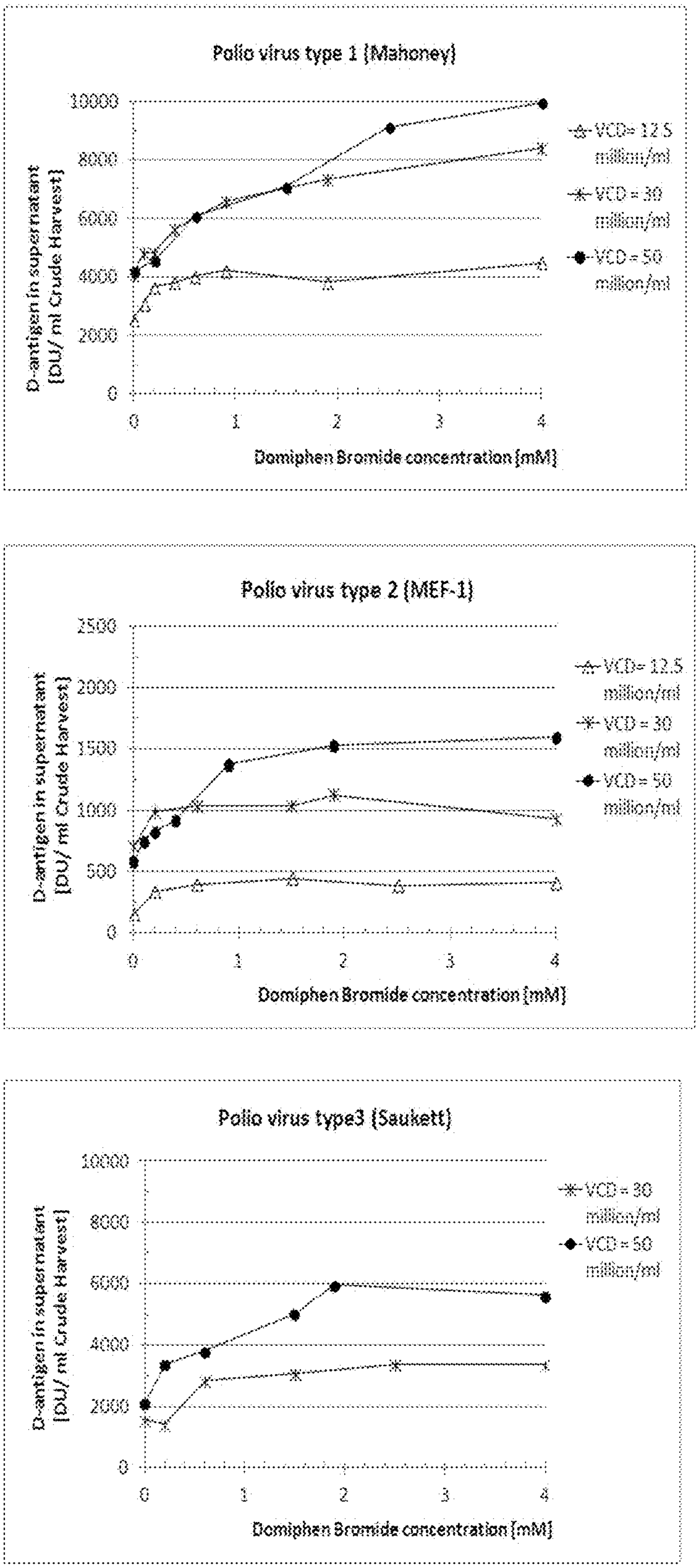
FIG. 1 (Panels A, B and C). D-antigen release from poliovirus-containing crude cell culture harvests as a result of the treatment with a detergent (Domiphen bromide). Several harvests with distinct cell densities, each containing a different polio strain (Mahoney, MEF-1 or Saukett), have been treated with a detergent and subsequently centrifuged. The D-antigen concentration in the supernatant is disclosed as a function of the detergent concentration.

This disclosure relates to improved methods of purifying poliovirus particles from a crude cell culture harvest-containing poliovirus. A crude cell culture harvest, as defined in this disclosure, is obtained immediately after cell culturing. It is referred to as "crude" because it has not been treated and has not been clarified in whatever form before being treated with a detergent. As opposed to the supernatant of a cell culture harvest, the crude cell culture harvest contains cells and cell debris, together with poliovirus particles.

In previously disclosed processes for poliovirus purification, e.g., in Henderson et al., a clarified harvest is treated as opposed to a crude cell culture harvest as described in the present application, the difference being that the harvest in Henderson et al. already went through a clarification step wherein the harvest was centrifuged to remove cell debris. In Henderson, a cationic detergent is not added to a crude cell culture harvest; instead, it is added to a clarified harvest from which cell debris has been previously removed.

In certain embodiments of this disclosure, the poliovirus particles are purified from high cell density crude cell harvests, leading to high yields of purified poliovirus. These high cell density, crude cell culture harvests are obtained by culturing cells to high cell densities. Such culturing can, for instance, be performed in batch, fed-batch or perfusion mode. Methods for culturing cells to high cell densities are known to the person skilled in the art. Specific methods for obtaining high cell density cultures are disclosed in, e.g., WO 2004/099396, WO 2005/095578, and WO 2008/006494.

According to this disclosure, a high cell density, crude cell culture harvest contains between about $5\times10^6$ and $150\times10^6$ cells/mL, e.g., between about $8\times10^6$ and $120\times10^6$ cells/mL, e.g., between about $12\times10^6$ and $100\times10^6$ cells/mL, e.g., between about $20\times10^6$ and $80\times10^6$ cells/m, e.g., between about $10\times10^6$ and $60\times10^6$ cells/mL.

In a preferred embodiment of this disclosure, the cell density in the crude cell culture harvest ranges between about $10\times10^6$ and $50\times10^6$ cells/mL, e.g., at least about $15\times10^6$ cells/mL, e.g., at least about $20\times10^6$ cells/mL, e.g., at least about $25\times10^6$, e.g., up to about $30\times10^6$ cells/mL, e.g., up to about $35\times10^6$ cells/mL, e.g., up to about $40\times10^6$ cells/mL, e.g., up to about $45\times10^6$ cells/mL.

However, the methods according to this disclosure also work for harvests from cell cultures with lower cell densities, e.g., between about $0.5\times10^6$ and $10\times10^6$ cells/mL, e.g., between about $1\times10^6$ and $5\times10^6$ cells/mL.

Typically, cell cultures are infected with poliovirus particles in order to allow the poliovirus to propagate in the cells. Herewith, crude cell culture harvests are obtained that contain high concentrations of poliovirus in a single bioreactor. Methods for infecting cell cultures are known to the person skilled in the art. Specific methods for obtaining high cell density cultures with high virus concentration are disclosed in, e.g., WO 2011/006823. This reference describes processes for the production of large quantities of recombinant poliovirus. These processes rely on the ability to infect cultures at high cell density with preservation of a high poliovirus productivity per cell. Herewith, it offers a method to obtain a high cell density crude cell culture harvest with high poliovirus concentrations in a single bioreactor. Typical yields of current processes for recombinant wild-type poliovirus, infected at a cell density of, e.g., 12.5 million/ml and harvested 22-24 hours post-infection are in the range from $5.0\times10^9$ to $3.2\times10^{10}$ TCID50/ml.

Once polioviruses have propagated in the cell culture, killing most of the cells (lysis), the poliovirus particles are, according to this disclosure, purified from the crude cell culture harvest.

Currently described processes for poliovirus production rely entirely on autologous release of poliovirus from the cells into the culture medium, which is a very efficient process for polioviruses. Surprisingly, it was found that a significant yield increase could be obtained when the cell culture (that already contained released poliovirus, cell debris, host cell DNA and host cell proteins) was treated with a detergent, preferably selected from the group of cationic detergents, anionic detergents, non-ionic detergents and zwitterionic detergents. In addition, this step resulted in a much cleaner clarified harvest with strongly reduced host cell DNA and protein.

Assays Used to Quantify Host Cell DNA, Host Cell Proteins and Poliovirus Particles During the Process Residual host cell DNA can be determined by real-time quantitative PCR, using quantitative Real-Time PCR with TAQMAN® probe. Primers and probe are designed for ribosomal 18S DNA. Quantities of sample DNA are determined by comparison to a DNA standard curve of known quantity that is prepared from producer cell DNA. The standard curve DNA stock is digested with the restriction enzyme Apa I to mimic sheared and partially degraded DNA.

DNA of samples is isolated by treatment with deoxycholic acid and Proteinase K. Real-Time PCR reactions are carried out using a Fast Real-Time PCR system (ABI Prism 7500). DNA quantities are derived from duplicate measurements of samples.

The concentration of residual host cell proteins (HCPs) was determined in a commercially available enzyme-linked immunosorbent assay (ELISA) kit (Cygnus Technologies, F530), specific for HCPs. The concentrations were determined in reference to the standard curve samples included in the kit. The range of the assay is 25-200 ng/ml.

Polio vaccines are based on live virus or inactivated virus. They contain the poliovirus D-antigen, which is the important protective antigen. Virus yields can be measured by standard virus titration techniques, while the determination of the D-antigen concentration for Mahoney, MEF-1 and Saukett poliovirus strains as a measure of potency can be performed by a D-antigen enzyme-linked immunosorbent assay (ELISA). The assay is based on the binding of the D-antigen to serotype-specific antibodies to which mixture peroxidase reagent is added. Peroxidase activity is then quantified by optical density. The D-antigen concentrations are determined in reference to international IPV standard from the European Directorate for the Quality of Medicines & HealthCare (EDQM), see Fuchs et al. The assay range is 40-160 DU/ml for Mahoney, 8-32 DU/ml for MEF-1 and 32-128 DU/ml for Saukett.

Immunogenicity can, for instance, be determined by in vivo testing in animals. Potency can be determined using the D-antigen ELISA and by a poliovirus neutralizing cell culture assay on sera from previously immunized rats.

Increased Release of D-antigen and Selective Precipitation of Host Cell DNA

It was found that the addition of a detergent to a poliovirus-containing crude cell culture harvest resulted in a substantial increase of the D-antigen concentration into the liquid phase of the harvest. At the same time, it causes host cell DNA to precipitate. As exemplified herein, this precipitation step resulted in an increase of about 100% in D-antigen release from the crude cell harvest into the liquid phase and resulted in a reduction in host cell DNA of about at least 5 log 10 following clarification.

Hence, this disclosure provides a method suited for purifying poliovirus particles from a crude cell culture harvest and is also suitable for a harvest from a culture with a high cell density. The detergents that may be useful in practicing this disclosure include, but are not limited to, cationic detergent, anionic detergents, non-ionic detergents and zwitterionic detergents.

In a preferred embodiment, the detergents that may be useful in practicing this disclosure are cationic detergents, which include, but are not limited to, amine copolymers, quaternary ammonium compounds such as, e.g., domiphen bromide (DB), Hexadecyltrimethylammonium bromide (CTAB), Hexadecylpyridinium chloride (CPC) and Benzethonium chloride (BTC), and any respective mixtures thereof. More specifically, the many forms of polyethylenimine (PEI) have shown to be very effective in neutralization of excess anionic charge (DNA impurities). Appropriate cationic detergents for use in this disclosure include, but are not limited to, the following classes and examples of commercially available products: monoalkyltrimethyl ammonium salts (examples of commercially available products include cetyltrimethylammonium chloride or bromide as CTAB, tetradecyltrimethylammonium bromide or chloride (TTA), alkyltrimethyl ammonium chloride, alkylaryltrimethyl ammonium chloride, dodecyltrimethylammonium bromide or chloride, dodecyldimethyl-2-phenoxyethylammonium bromide, hexadecylamine chloride or bromide salt, dodecyl amine or chloride salt, and cetyldimethylethyl ammonium bromide or chloride), monoalkyldimethylbenzyl ammonium salts (examples include alkyldimethylbenzyl ammonium chlorides and benzethonium chloride as BTC), dialkyldimethyl ammonium salts (commercial products include domiphen bromide (DB), didecyldimethyl ammonium halides, and octyldodecyldimethyl ammonium chloride or bromide), heteroaromatic ammonium salts (commercial products include cetylpyridium halides (CPC or bromide salt and hexadecylpyridinium bromide or chloride), cis-isomer 1-[3-chloroallyl]-3,5,7-triaza-1-azoniaadamantane, alkyl soquinolinium bromide, and alkyl dimethylnaphthyl-methyl ammonium chloride (BTC 1110), polysubstituted quaternary ammonium salts, (commercially available products include, but are not limited to alkyldimethylbenzyl ammonium saccharinate and alkyldimethylethylbenzyl ammonium cyclohexylsulfamate), bis-quaternary ammonium salts (product examples include 1,10-bis(2-methyl-4-aminoquinolinium chloride)-decane, 1,6-bis [1-methyl-3-(2, 2,6-trimethyl cyclohexyl)-propyldimethyl ammonium chloride] hexane or triclobisonium chloride, and the bis-quat referred to as CDQ by Buckman Brochures), and polymeric quaternary ammonium salts (includes polyionenes such as poly[oxyethylene(dimethyliminio)ethylene(dimethyliminio)-ethylenedichloride], poly [N-3-dimethylammonio)propyl]N-[3-ethyleneoxyethylenedimethylammonio)propyl] urea dichloride, and alpha-4-[1-tri s(2-hydroxyethyl) ammonium chloride).

The skilled person will understand that these are examples of cationic detergents, and based on the disclosure described herein, it is clear that these will also be suitable in this application.

In an even more preferred embodiment, dialkyldimethylammonium salts such as domiphen bromide (DB) are used in this disclosure. Though a large number of potential cationic detergents can be used to practice this disclosure, domiphen bromide is of particular interest due primarily to its availability as a GMP grade raw material and current use in other products intended for human use. More specifically, since domiphen bromide is extensively used as an active ingredient in oral hygiene products as well as topical antibiotic creams, this molecule is produced in large quantities and released under cGMP conditions.

In another preferred embodiment, the detergents that may be useful in practicing this disclosure are anionic detergents, which include, but are not limited to, alkyl sulfonates such as Sodium taurodeoxycholate hydrate (STH), 1-Octanesulfonic acid sodium salt, Sodium 1-decanesulfonate, Sodium 1-heptanesulfonate and Sodium hexanesulfonate; and alkyl sulphates such as Sodium dodecyl sulfate (SDS), Lithium dodecyl sulfate and Sodium octyl sulphate; and any respective mixtures thereof.

In yet another preferred embodiment, the detergents that may be useful in practicing this disclosure are zwitterionic detergents that include, but are not limited to, 3-(N,N-Dimethylmyristylammonio)propanesulfonate (SB3-14), 3-[(3-Cholamidopropyl)dimethylammonio]-1-propanesulfonate (CHAPS), 3-[(3-Cholamidopropyl]dimethylammonio)-2-hydroxy-1-propanesulfonate (CHAPSO), 3-(N,N-Dimethyloctylammonio)propanesulfonate inner salt (SB3-8), 3-[N,N-Dimethyl(3-palmitoylaminopropyl)ammonio]-propanesulfonate, 3-(N,N-Dimethyloctadecylammonio) propanesulfonate (SB3-18), Amidosulfobetaine-14; 3-[N,N-Dimethyl(3-myristoylaminopropyl)ammonio] propanesulfonate (ASB-14) and N,N-Dimethyldodecylamine N-oxide (DDAO); and any respective mixtures thereof.

In another preferred embodiment, the detergents that may be useful in practicing this disclosure are non-ionic detergents that include, but are not limited to, poly(oxyethylene) ethers such as 4-(1,1,3,3-Tetramethylbutyl)phenyl-polyethylene glycol (TRITON® X-100), Polyethyleneglycol hexadecylether (BRIJ® 58), Polyethyleneglycol sorbitan monooleate (TWEEN®80), (1,1,3,3-Tetramethylbutyl)phenyl-polyethyleneglycol (TRITON® X-114), Polyoxyethylenesorbitan monolaurate (TWEEN®20), Polyethylene glycol dodecyl ether (Thesit); Glycosidic detergents such as Decyl-β-D-1-thiomaltopyranoside (DTP), 6-Cyclohexylhexyl β-D-maltoside (Cymal-6), Decyl-β-D-1-thioglucopyranoside, n-Dodecyl β-D-maltoside (DDM), Octyl β-D-glucopyranoside (OGP), Octyl β-D-1-thioglucopyranoside; Bile acids such as N,N-Bis[3-(D-gluconamido)propyl]deoxycholamide (Deoxy-BigCHAP); and any respective mixtures thereof.

The appropriate concentration of detergent for treating a poliovirus containing high cell density suspension comprising a cell density ranging between $10\times10^6$ and $150\times10^6$ cells/mL ranges between about 1 mM and 12 mM. The appropriate concentration of DB for treating a poliovirus-containing high cell density suspension comprising a cell density ranging between $10\times10^6$ and $50\times10^6$ cells/mL ranges between about 1 mM and 4 mM. The appropriate concentration of DB for treating a poliovirus-containing high cell density suspension harvest comprising a cell density ranging between $10\times10^6$ and $30\times10^6$ cells/mL ranges between about 1 and 3 mM.

It will be within the purview of the skilled man in the art to test potential substitutes for the detergents disclosed herein to identify a compound that effectively increases release of poliovirus from the cells, while it may further precipitate nucleic acid molecules and other cellular debris away from poliovirus particles as exemplified herein for Hexadecyltrimethylammonium bromide (CTAB), Hexadecylpyridinium chloride (CPC), Benzethonium chloride (BTC) and domiphen bromide (DB) and at the same time effectively precipitates nucleic acid molecules and other cellular debris away from poliovirus particles.

Therefore, this disclosure relates in part to methods of purifying poliovirus particles from a high cell density suspension while simultaneously enhancing virus recovery. The methods enhance the release of poliovirus particles and at the same time result in the selective precipitation of host cell nucleic acid molecules away from the poliovirus particles by adding a detergent to the crude cell culture harvest.

Methods of Clarification

The crude cell culture harvest treated with a detergent is subsequently clarified to remove whole cells, precipitated host cell DNA, cell debris and other impurities. Said clarification can be performed by depth filtration. Centrifugation with or without polishing depth filtration is also feasible. Therefore, the clarification of detergent-treated harvest may be accomplished using centrifugation alone, or centrifugation in tandem with a polishing clarification step such as depth filtration.

In choosing a filter or filter scheme, it is preferred to ensure a robust performance in the event upstream changes or variations occur. Maintaining the balance between good clarification performance and step yields can be investigated by testing a variety of filter types with varying internal media. Suitable filters may utilize cellulose filters, regenerated cellulose fibers, cellulose fibers combined with inorganic filter aids (e.g., diatomaceous earth, perlite, fumed silica), cellulose fibers combined with inorganic aids and organic resins, or any combination thereof, and polymeric filters (examples include, but are not limited to, nylon, polypropylene, polyethersulfone) to achieve effective removal and acceptable virus recoveries. In general, a multiple stage process is preferable but not required. An exemplary two or three-stage process would consist of a coarse filter(s) to remove large precipitate and cell debris followed by polishing second stage filters(s) with nominal pore sizes greater than 0.2 μm but less than 1 μm. The optimal combination will be a function of the precipitate size distribution as well as other variables. In addition, single stage operations employing a relatively tight filter or centrifugation may also produce a product of good quality. More generally, any clarification approach including dead-end filtration, microfiltration, centrifugation, or body feed of filter aids (e.g., diatomaceous earth) in combination with the dead-end or depth filtration, which provides a filtrate of suitable clarity to not foul the membrane and/or resin in the subsequent step, will be acceptable to practice within this disclosure. Depth filtration shows a robust method of primary clarification for this disclosure.

In another preferred embodiment according to this disclosure, an in-line anionic exchange membrane can be integrated in the clarification filter train to further remove residual level of DNA or negatively charged impurities, like host cell proteins without loss of poliovirus under physiological conditions. These high-capacity membranes with high pores (>3 um) are well known to effectively remove negatively charged contaminants like residual DNA, host cell proteins and/or adventitious viruses in, for example, the monoclonal antibody production field. Suitable membranes are, among others, strong anionic exchange membranes with positively charged ligand, typically quaternary ammonium grated to, for example, a cross-linked cellulose matrix.

Surprisingly, it was found that albeit typically viruses bind to these membranes under physiological conditions (pH 7-8, conductivity 15-18 mS/cm), the poliovirus with a somewhat higher net isoelectric point flows through these membranes, which makes it a suitable choice for negatively charged impurity removal. In certain embodiments, chromatographic bead-based resins can be used but because of the advantage of high convective flows, membranes are the preferred choice.

The combination of the detergent treatment and clarification steps results in a reduction in host cell DNA of at least 4 log 10, preferably of at least 5 log 10, or even more preferably of at least 5.5 log 10. The overall pressure build up across the complete filter set up remained below 0.8 bar, indicative for people skilled in the art that the filter types have been adequately selected and sized.

In a preferred embodiment, an anion exchange membrane can be integrated in the clarification filter train, eliminating the need for a dedicated anionic exchange step, which is present in all currently known poliovirus manufacturing processes.

In preferred embodiments of the disclosure, harvested virus particles are treated by the multi-stage clarification process flow that includes (in subsequent order): depth filtration via a charged filter unit (e.g., a MILLIPORE® MILLISTAK® DOHC filter), dual membrane filter 0.8 μm/0.45 μm (e.g., SARTOPORE® 2), a strong anionic exchange adsorption membrane (e.g., a SARTORIUS® Single Sep Q) and a sterile membrane filtration with relatively small pore size (e.g., 0.22 μm filter units).

Steps for Further Purification

Following clarification, concentration of the clarified virus particle suspension can be considered as a further step in the method according to this disclosure, but is by no means essential. Concentration of the virus particle suspension can be performed by ultrafiltration. The suspension can be concentrated 5 to 20 times (and possibly be treated with nuclease, as mentioned hereinbelow). The particular ultrafiltration membrane selected will be of a size sufficiently small to retain virus particles but large enough to effectively clear impurities. Depending on the manufacturer and membrane type, nominal molecular weight cutoffs between 10 and 1000 kDa may be appropriate. The choice of molecular size cutoff is dictated by the tradeoffs between yield and impurity clearance. Ultrafiltration using tangential flow mode is preferred. In this mode, the step may be controlled by setting a fixed cross-flow with or without backpressure on the retentate, setting a fixed transmembrane pressure, or fixing both the cross-flow and the permeate flux.

Another process step that can be included at this stage of the process, but that is by no means essential, is the subsequent introduction of a buffer exchange process step via diafiltration. Diafiltration, or buffer exchange, using ultrafiltration units is used for removal and exchange of salts, sugars and the like. The person skilled in the art knows under which conditions the buffer exchange should take place and which buffers are appropriate for this step.

Nuclease treatment can also be considered for inclusion in the process at this stage of the process, but is by no means essential. Nuclease treatment can include the use of a broad spectrum of nucleases, e.g., BENZONASE®, a DNase, an RNase, or any combination thereof. A nuclease or cocktail with both RNase and DNase activity is often used. A nuclease treatment step can be contemplated at any point in the process, as long as residual nuclease content in the final product is acceptable to the application. The nuclease treatment may occur after clarification alone or after clarification and a concentration step, but before a further purification step such as a capture or polishing step.

An additional unit operation that can be used for impurity reduction could, for example, be a chromatography unit, but is by no means essential to the process. The chromatography unit consisting of chromatography media in different formats such as resins, membrane adsorbers and monoliths can be used. The chromatography unit operation(s) can be operated in either positive or negative mode (explained below). In certain embodiments of the disclosure, the virus particle suspension fed to the chromatography unit(s) can be adjusted to certain feed conditions such as, e.g., pH and/or ionic strength of the solution. During this step, virus particles are further purified by separating the virus particles from the remaining impurities such as, e.g., host cell nucleic acids and host cell proteins. Purification of virus particles during this step can be achieved by, e.g., affinity chromatography, anion exchange chromatography, cation exchange chromatography, size exclusion chromatography, reversed phase chromatography, hydrophobic chromatography, mixed mode chromatography and/or hydroxyapatite chromatography, either used as a stand-alone process step or in a combination with several process steps.

In certain embodiments of this disclosure, where chromatography unit operation(s) are used, virus particles can be purified by separating them from the remaining impurities in the virus particle suspension. Virus particles can be either separated by binding the virus particles at certain conditions to the chromatography media whereas some, if not most of the impurities, are not bound to the chromatography media. Otherwise, virus particles can be separated by binding some, if not most of the impurities to the chromatography media leaving most of the virus particles unbound to the chromatography media. Above-mentioned operating modes are known in the art as positive binding mode and negative binding mode, respectively.

It is also possible to operate certain chromatography unit operation(s) without any binding interaction depending on the chromatography media used. Exemplary chromatography media can be, but in no way limited to, size exclusion chromatography media (e.g., SEPHAROSE® 6FF). The person skilled in the art knows how to determine the required conditions for separating virus particles from the impurities. Examples of the sequential use of different unit operations to achieve highly purified polio virus solutions as above are described in literature, for instance, in Bakker et al., 2011, and Thomassen et al., 2013.

In certain embodiments of the disclosure, chromatography unit operation(s) can be used as the capture step, which is, in essence, a combination of a concentration and purification step, herewith eliminating the need for a stand-alone concentration step as described previously (e.g., an ultrafiltration step). Chromatography media in different formats can be used in capture steps. Examples of chromatography media formats are a.o. resins, membrane adsorbers and monoliths. The person skilled in the art can easily determine the optimal chromatography media format to be used for a particular process step.

In certain embodiments of the disclosure, where chromatography unit operation(s) are used as capture step(s), virus particles can be purified by separating them from the remaining impurities in the virus particle suspension. Virus particles can be separated by binding the virus particles at certain conditions to the chromatography media whereas some, if not most, of the impurities are not bound to the chromatography media.

In certain embodiments of the disclosure, where chromatography unit operation(s) are used as capture step(s), virus particle suspension, also referred to as the "feed material," needs to be adjusted to certain conditions for optimal separation from the impurities. Exemplary conditions of the feed material to be adjusted are, e.g., pH and ionic strength of the virus particle suspension. The virus particles can be further purified by the subsequent elution step that can be achieved by, e.g., changing the pH and/or ionic strength of the liquid phase of the chromatography medium.

In a particular embodiment of the disclosure, a cationic exchange chromatography medium is used as a capture step. The conditions of the feed material can be adjusted by addition of acids or bases (e.g., Citric Acid, NaOH) to reach desired pH and by addition of salt solutions or de-ionized water (e.g., NaCl or MILLI-Q®) to reach desired ionic strength. As a guide and certainly not a limitation, the pH could potentially range from about 4.5-7.0 and ionic strength can potentially range from about 10 mS/cm-25 mS/cm. An extra clarification step (e.g., 0.45 μm or 0.22 μm filtration) after the feed material adjustment can be considered for inclusion in the process, in order to reduce the burden on the following chromatography step, but is by no means essential. The person skilled in the art can easily determine what solutions and filtration units to use for the particular process step.

In particular embodiments of the disclosure, where chromatography unit operation(s) are used as capture step(s) and where virus particles are selectively bound to strong cationic exchange chromatography media for separation, further virus particle purification is achieved by the subsequent selective elution of the virus particles by changing conditions of the liquid phase within the unit operation. As a guide and certainly not a limitation, elution of virus particles can be achieved by changing the pH of the liquid phase from acidic pH values to basic pH values (e.g., ranges between pH 4-10). As a guide and certainly not a limitation, elution of virus particles can also be achieved by changing the ionic strength of the liquid phase from lower to higher ionic strength (e.g., ranges between 10 mS/cm-35 mS/cm).

In a preferred embodiment of the disclosure, a poliovirus particle suspension, also referred to as feed material, is adjusted to an acidic pH ranging from 4.4 to 5.6 and an ionic strength ranging from 14 mS/cm to 22 mS/cm. Subsequently, adjusted feed material is loaded to a cation exchange chromatography membrane adsorber (e.g., SARTOBIND® S) where the virus selectively binds to the membrane. Virus particles are further purified from impurities in the following elution step by increasing the ionic strength of the elution buffer into the range between 25 mS/cm-40 mS/cm while maintaining the pH range constant between 4.4-5.6. Eluted virus particle suspension can subsequently be filtered through a, e.g., 0.22 μm filtration unit in order to reduce bioburden and precipitants.

According to this disclosure, if it is necessary for achieving a certain product purity, an additional purification step, called the "polishing" step, can be incorporated in the process. The "polishing" step is by no means essential in the whole purification process flow, but it is a preferred process step for achieving robustness in the whole purification process flow.

During this step, it is desired to remove trace amounts of impurities such as, e.g., but not limited to, host cell nucleic acids (e.g., DNA) and host cell proteins from the virus particle suspension. The "polishing" step can be achieved by, but is certainly not limited to, affinity chromatography, anion exchange chromatography, size exclusion chromatography, reversed phase chromatography, hydrophobic chromatography, mixed mode chromatography, hydroxyapatite chromatography and/or ultrafiltration, either used as a stand-alone process step or in a combination of several process steps. During this step, buffer exchange of the virus suspension can be considered for inclusion to the process flow, but is by no means essential.

In certain embodiments of the disclosure, where chromatography unit operation(s) are used as polishing step(s), chromatography media in different formats such as, e.g., resins, membrane adsorbers and monoliths can be used. The chromatography unit operation(s) can be operated in either positive or negative mode. In certain embodiments of the disclosure, the virus particle suspension fed to the polishing step(s) can be adjusted to certain feed conditions such as, e.g., pH and/or ionic strength of the solution. The virus particles can be purified by a subsequent elution step that can be achieved by, e.g., changing the pH and/or ionic strength of the liquid phase of the chromatography medium.

In particular embodiments of the disclosure, virus particle purification can also be achieved by exploitation of size differences between the virus particles and the impurities. Exemplary process steps can be size exclusion chromatography and/or ultrafiltration.

In particular embodiments of the disclosure, polishing step(s) can, in addition to purifying the virus particles, be used as buffer exchange steps. Exemplary process steps can be, but not limited to, size exclusion chromatography and/or diafiltration.

In particular embodiments of the disclosure, where ultrafiltration/diafiltration steps are incorporated, removal of residual impurities (e.g., host cell proteins, host cell nucleic acids) as well as exchanging the buffer to the desired buffer (e.g., formulation buffer) can be achieved. Tangential flow ultrafiltration is useful in removing residual protein and nucleic acid and to exchange the virus particles into a formulation buffer. The selected ultrafiltration membrane will be of a size sufficiently small to retain virus particles but large enough to effectively clear impurities. Depending on the manufacturer and membrane type, nominal molecular weight cutoffs between 100 and 1000 kDa may be appropriate.

In preferred embodiments of the disclosure, virus particles can be separated from residual impurities by size exclusion chromatography (e.g., SEPHAROSE® 6FF) while concurrently, the buffer is exchanged to a formulation buffer. Desired levels of virus particle purity, as well as buffer exchange quality, can be achieved by altering several variables of the size exclusion chromatography unit. The person skilled in the art can determine the optimal operating conditions in order to achieve the required purity and process performance specifications.

A particularly preferred method to obtain purified poliovirus from cell culture according to the disclosure comprises the steps of: a) adding a detergent to the cell culture; b) clarifying the poliovirus-containing cell culture to obtain a clarified harvest with poliovirus particles; c) subjecting the clarified harvest obtained in step b) to a cationic exchange chromatography step to obtain a poliovirus-containing suspension; and d) further purifying the poliovirus from the poliovirus-containing suspension by size exclusion chromatography.

A sterile filtration step may be included at the end of the process in order to reduce bioburden; such step is by no means essential. The product can be filtered through a 0.22 µm modified polyvinylidene fluoride (PVDF) membrane (e.g., MILLIPORE® MILLIPAK®).

Scale of Cell Culture Systems and Downstream Processing Systems

The processes of this disclosure are scalable. The cell cultures for which this disclosure can be used range from small-scale cultures (e.g., 1-10 liter runs) to medium scale cultures (e.g., 20-1000 L runs) up to large commercial-scale preparations, such as 1000 to 50,000 L production runs. The initial process steps such as depth filtration scale with culture volume while the cationic exchange chromatography or alternative capture step and subsequent steps scale with poliovirus particle amount. Therefore, the batch size of the latter steps will be based on a bioreactor productivity estimate of at least $5\times10^9$ TCID50/m1 and up to about $1\times10^{11}$ TCID50/ml. These high poliovirus yields can, for instance, be obtained by infecting high cell density cultures (as described, e.g., in WO 2011/006823). The further purification of these high density cell suspensions containing high concentrations of poliovirus particles is made possible with this disclosure. The possibility to process these suspensions, which contain high amounts of cell debris and host cell impurities allow for the purification of high quantities of poliovirus particles per volume of suspension. It is the merit of this disclosure to provide for a method for processing cell culture batches with high cell densities, containing high concentrations of poliovirus particles and therewith allowing for very high virus yields per processed volume. The present method, although it is applicable to large-scale cell cultures will allow for cells to be cultured at a smaller scale, yet to higher cell densities and still reach high poliovirus yields that can be efficiently further processed. This method offers the possibility to process highly concentrated poliovirus batches that will have a great impact on the entire poliovirus purification industry.

Poliovirus and Producer Cells

A polio vaccine can be monovalent, containing one type of poliovirus (type 1, 2 or 3), or divalent (containing two types of poliovirus, e.g., types 1 and 2, 1 and 3 or 2 and 3), or trivalent (containing three types of poliovirus, i.e., types 1, 2 and 3).

It is possible to produce IPV from wild-type polioviruses. Alternatively, IPV may be produced from non-virulent live poliovirus, e.g., from the Sabin strains, which would further reduce the risk of reintroducing wild-type poliovirus from IPV manufacturing (see, e.g., WO 2007/007344, and Doi et al., 2001). This disclosure is suitable for the purification of wild-type poliovirus (types 1, 2 and 3, e.g., the type 1 strain Mahoney, type 2 strain MEF-1, or type 3 strain Saukett) as well as of non-virulent types of poliovirus (e.g., the Sabin strains). The processes according to the disclosure applied to produce IPV may serve to drive the cost down to such an extent that IPV may become available to less- and least-developed countries. Although, in general, OPV is cheaper than IPV when prepared according to conventional methods, the highly efficient processes of the disclosure can still reduce the costs of the bulk material for OPV and, hence, reduce the costs thereof as well.

In general, each of the poliovirus strains is cultured in a separate batch and if, for instance, a trivalent vaccine containing three types of poliovirus is prepared, the (inactivated, for IPV) viruses are mixed and formulated for preparation of individual dosages. In certain embodiments, for example, a final vaccine per dose (e.g., 0.5 ml) may, for instance, comprise 40 D-antigen units (DU) of type 1 poliovirus, 8 DU of type 2 poliovirus and 32 DU of type 3 poliovirus, determined by comparison to reference preparations.

The method according to this disclosure can be applied to cell culture harvest from distinct cell types. One type of cells that can be used in the methods of this disclosure are PER.C6® cells, which are immortalized cells, also known in the art as continuous cell lines, and as such, have the potential for an infinite lifespan (see, e.g., Barrett et al., 2009). For the purpose of the present application, "PER.C6® cells" shall mean cells as deposited under ECACC no. 9602240 on 29 Feb. 1996. It will be clear to the skilled person that this definition will include cells from an upstream or downstream passage or a descendent of an upstream or downstream passage of these deposited cells. PER.C6® cells are described in U.S. Pat. No. 5,994,128 and in Fallaux et al., 1998. These cells are very suitable for poliovirus production to produce cell-based poliovirus vaccines, since they can be infected and propagate the virus with high efficiency, such as, for instance, described in WO 2011/006823. It is demonstrated herein that these cells are also very suitable for production of poliovirus to high levels in serum-free suspension cultures.

Since other cell types can be used to propagate polioviruses, the methods of this disclosure are also applicable to process poliovirus-containing crude cell harvests comprising other cell types. As exemplified herein, harvests from Vero cells and MRC-5 cells were processed with the methods of this disclosure.

For large-scale manufacturing of inactivated polio vaccines, poliovirus is generally propagated on adherent Vero cells, which are monkey-derived. Vero cells, which are cultured on microcarriers, are widely used for vaccine production, including inactivated as well as live attenuated polio vaccines, and thus far, are the most widely accepted continuous cell lines by regulatory authorities for the manufacture of viral vaccines, and use of these cells for vaccine production is expected to rise by experts in the field (Barrett et al., 2009). Large-scale microcarrier culture of Vero cells for inactivated poliovirus vaccine has been described by Montagnon et al., 1982 and 1984. A process for the large-scale production of a polio vaccine using Vero cells, and the resulting vaccine, are also described in U.S. Pat. No. 4,525,349.

High titers of poliovirus (Sabin type 1) production (almost $2\times10^9$ $TCID_{50}$/ml) have been obtained in Vero cells cultured on microcarriers in serum-containing medium prior to the virus production phase, which took place in serum-free medium (Merten et al., 1997). In view of the disadvantages of using serum, the authors have indicated that a completely serum-free process is desired. Under serum-free conditions, a poliovirus production titer of $6.3\times10^8$ $TCID_{50}$/ml was obtained. The poliovirus production titers obtained by the method of this disclosure on PER.C6® cells were ranging between $5.0\times10^9$ to $3.2\times10^{10}$ TCID50/ml (at a cell density at infection of 12.5 million/ml).

A conventional alternative cell platform commonly used for vaccine production, in general, and IPV production, in particular, are Human Fetal Lung Fibroblast Cells (MRC-5 cells) initiated by J. B. Jacobs, 1966. A host cell line comparison study (Vlecken et al., 2013) showed that adherent MRC-5 and VERO cell lines are the highest producers among an extended host cell panel, which makes them suitable candidates for viral vaccine production. Using flask surface adherent cultures, virus titers achieved were (0.7-2.6)$\times10^6$ TCID50/ml and (1.4-5.8)$\times10^6$ TCID50/ml for MRC-5 and Vero cell cultures, respectively.

The purification methods of the disclosure are suitable for poliovirus propagated in any cell type amenable for poliovirus propagation, i.e., the methods of the disclosure are independent from the cell type used for growing poliovirus.

The disclosure is further explained in the following examples. The examples do not limit the disclosure in any way. They merely serve to clarify the disclosure.

EXAMPLES

Example 1

Increased Poliovirus Purification Yields from Poliovirus-containing Crude Cell Culture Harvest by Addition of a Cationic Detergent Cells from the PER.C6® cell line were grown in a serum-free culture medium in a 10 L bioreactor operated in perfusion mode to a cell density of approximately $50\times10^6$ viable cells/ml (vc/ml). Prior to infection with poliovirus type 1 (Mahoney), type 2 (MEF-1) or type 3 (Saukett), the culture was diluted with fresh culture medium to viable cell density in the range between $12.5\times10^6$ and $50\times10^6$ vc/mL. The batch infection process took place in 10 L bioreactors at 35° C. at a multiplicity of infection of 1. At the time of harvest, 20-24 hours post-infection, a 50 ml sample was taken, which was subsequently distributed in 11 aliquots of 4 mL.

In order to determine the effect of a detergent on the poliovirus-containing cell culture harvests, a titration experiment was performed with Domiphen bromide (DB). A discrete amount of DB stock solution was added to the sample aliquots at a targeted DB concentration (between 0 and 4 mM). The samples were mixed and incubated for one hour at 35° C. Subsequently, the samples were centrifuged for 5 minutes at 3000 g to spin-down the precipitated DNA. Supernatant samples were analyzed for virus quantity by D-antigen ELISA, and for host cell DNA using Q-PCR.

FIG. 1 (Panels A, B and C) shows D-antigen release from poliovirus-containing cell culture harvests as a result of the treatment with a detergent (DB). Several harvests with distinct cell densities and each containing a different polio strain (Mahoney, MEF-1 or Saukett) have been treated with a detergent and subsequently centrifuged. The D-antigen concentration in the supernatant, which is corrected for the detergent addition dilution, is given as a function of the detergent concentration. FIG. 1 shows that after the addition of a detergent (DB), the virus titer increased substantially as compared to before the addition of a detergent (DB). For each strain and for each viable cell density, the same pattern can be observed, i.e., increasing the detergent (DB) concentration leads to increased virus release from the crude cell harvest into the liquid phase.

Figure 2:
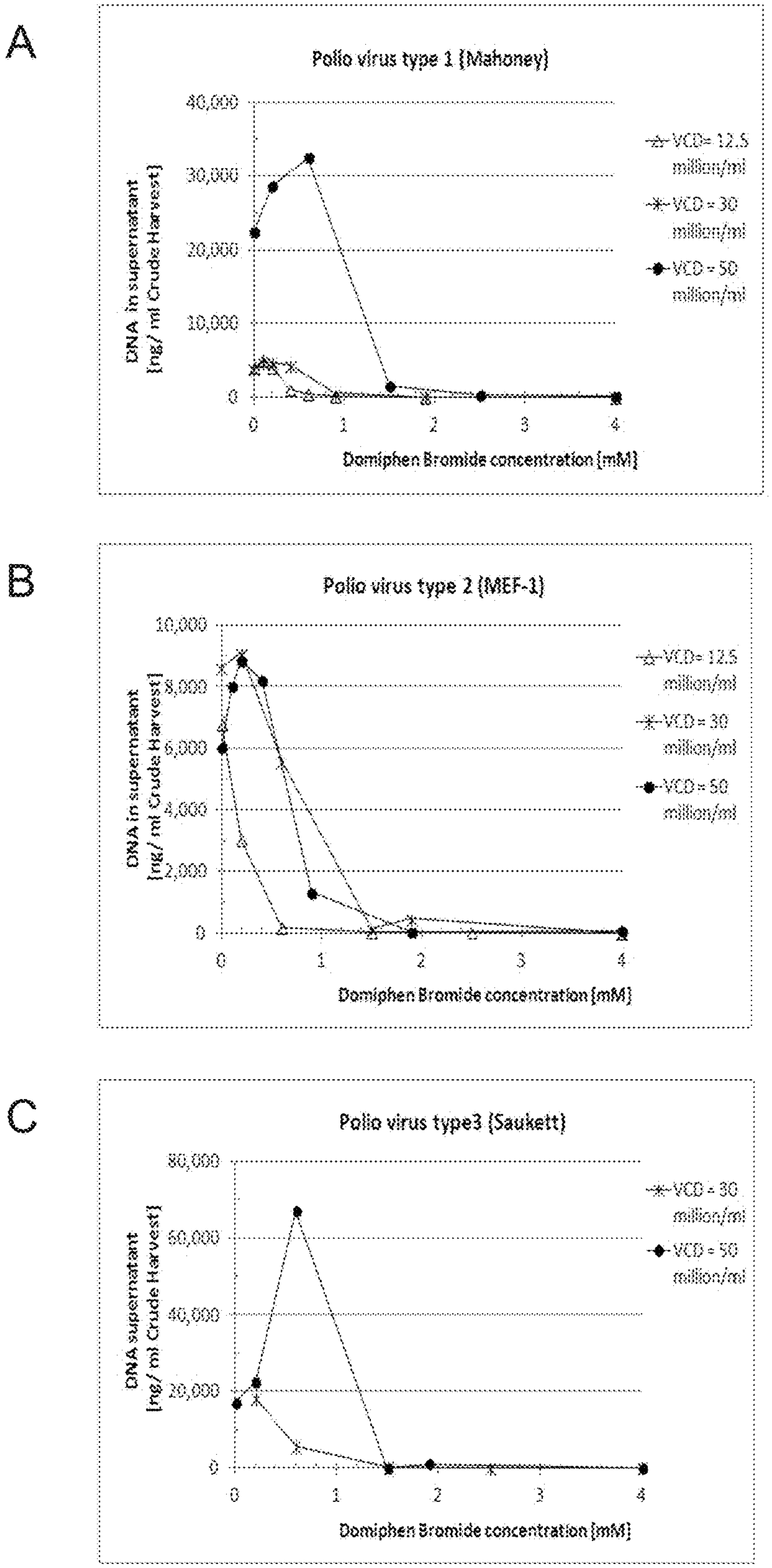
FIG. 2 (Panels A, B and C). Host cell DNA precipitation in poliovirus-containing crude cell culture harvests as a result of the treatment with a detergent (Domiphen bromide). Several harvests with distinct cell densities and each containing a different polio strain (Mahoney, MEF-1 or Saukett) have been treated with a detergent and subsequently centrifuged. The host cell DNA concentration in the supernatant is disclosed as a function of the detergent concentration.

FIG. 2 (Panels A, B and C) shows host cell DNA precipitation in poliovirus-containing crude cell culture harvests as a result of the treatment with a detergent (Domiphen bromide). The concentrations on the y-axis have been corrected for the detergent dilution factor. For each strain and for each viable cell density, host cell DNA is precipitated from the crude cell culture harvest. FIG. 2 clearly indicates that effective DNA clearance occurred in the aliquots for detergent (DB) concentrations above 1.3 mM.

Also, a minimum DB concentration could be determined from each individual curve (FIGS. 1 and 2), for which a plateau level of D-antigen is obtained and at the same time, maximum DNA clearance is obtained. This minimum amount of detergent increases with cell density to accommodate for higher amounts of cells and increased level of soluble host cell DNA in the medium.

Since the increase of detergent did not lead to poliovirus precipitation, a person skilled in the art would extrapolate these results to poliovirus-containing cell suspensions of even higher cell densities, e.g., of about $70\times10^6$ cells/mL, e.g., of about $90\times10^6$ cells/mL, e.g., up to about $120\times10^6$ cells/mL, e.g., up to about $150\times10^6$ cells/mL. The skilled person would conclude that the poliovirus from such high cell density crude cell culture harvests can be purified by the methods of this disclosure.

Example 2

Efficacy of Detergent Treatment on Poliovirus Release From VERO and MRC-5 Crude Cell Culture Harvests Treatment of a Crude Poliovirus Harvest from an Adherent VERO Cell Culture Vero cells were pre-cultured in T-175 flasks and scaled up to inoculate 1 spinnerflasks Cytodex 3, at $30\times10^3$ cells/$cm^2$ in VERO spinner medium (MEM+10% FBS+6 mM Glutamine+4.6 g/L Glucose) and 5 g/L microcarriers Cytodex 3. The cells were incubated at 37° C., 5% $CO_2$ and stirred at 60 rpm for the first 24 hours and at 90 rpm during the following days. At day 3 post-seeding (on microcarriers), the cells were washed with pre-warmed PBS and a medium change was performed with infection medium (MEM+4 mM Glutamine). The replenished cell culture was distributed over 50 ml tubespins containing 20 ml cell culture seeded at $1\times10^6$ cells/mL. The tubespins were infected for each of the three virus strains (Mahoney, MEF-1, Saukett) with an MOI of 1. Infection was performed at 35° C., 170 rpm, 5% $CO_2$ and the virus was harvested 72 hours post-infection. In order to determine the effect of a detergent on the poliovirus-containing crude VERO cell harvests grown on microcarriers, a DB stock solution was added to the harvest at a final concentration of 1.6 mM. For this experiment, a DB stock solution (1.05% w/v, 40 mM NaCl) was used. The samples were mixed and incubated for one hour at 35° C. Subsequently, the samples were centrifuged for 5 minutes at 3000 g to spin down the precipitated DNA. Supernatant samples were analyzed for virus quantity by D-antigen ELISA and for host cell DNA using Q-PCR.

Treatment of a Crude Poliovirus Harvest from an Adherent MRC-5 Cell Culture

MRC-5 cells were cultured in BME+10% FBS (nHI)+4 mM Glutamine and incubated at 37° C. and 10% $CO_2$ in a T75 flask. Every 3 to 4 days, when cultures were approximately 80-90% confluent, MRC-5 cultures were passaged and expanded into T-175 flasks. When the cells reached a density of about 80-90% (day 4), the cells were washed with PBS and a medium change was performed with BME+4 mM Glutamine. T-175 flasks were infected for each of the three virus strains (Mahoney, MEF-1, Saukett) with an MOI of 1, in a total volume of 25 ml per flask. The infection was performed at 35° C., 10% CO2 and the virus was harvested 72 hours post-infection. In order to determine the effect of a detergent on the poliovirus-containing crude MRC-5-adherent cell harvests, a DB stock solution was added to the harvest at a final concentration of 0.6 mM. The samples were mixed and incubated for one hour at 35° C. Subsequently, the samples were centrifuged for 5 minutes at 3000 g to spin down the precipitated DNA. Supernatant samples were analyzed for virus quantity by D-antigen ELISA and for host cell DNA using Q-PCR.

TABLE 1

D-antigen concentration in supernatant of cell culture harvest [DU/ml]

| | Vero-adherent cell culture grown on microcarriers | | MRC-5-adherent cell culture grown on T-175 flasks | |
|---|---|---|---|---|
| | DB concentration | | | |
| | 0 mM | 1.6 mM | 0 mM | 0.6 mM |
| Type 1 (Mahoney) | 153 | 160 | 30 | 36 |
| Type 2 (MEF-1) | 19 | 34 | 8 | 13 |
| Type 3 (Saukett) | 106 | 119 | 11 | 16 |

Table 1 shows the concentration of D-antigen upon DB treatment, at a DB concentration of 1.6 mM for VERO cell poliovirus harvests and 0.6 mM for MRC-5 cell poliovirus harvests. The D-antigen concentrations in the table are corrected for dilution caused by the detergent addition.

The results show that the addition of detergent (DB) caused additional virus to be released in the liquid phase of the VERO and MRC-5 cell culture harvests, whereas DNA is precipitated away from the virus. Indeed, DNA clearance at 1.6 mM DB was more than 2 log 10 in the VERO cell culture. DNA clearance at 0.6 mM DB was more than 3 log 10 in the MRC-5 cell culture (data not shown). This demonstrates that the disclosure is applicable for various cell types used for poliovirus production.

Example 3

Impact of Detergent Treatment on Poliovirus Release and DNA Clearance in a Bioreactor Prior to Cell Clarification PER.C6® cells were grown in a serum-free culture medium in a 10 L glass bioreactor operated in perfusion mode to a cell density of approximately $50\times10^6$ vc/ml. Prior to infection with poliovirus type 1 (Mahoney), type 2 (MEF-1) or type 3 (Saukett), the culture was diluted with fresh culture medium to a viable cell density of $12.5\times10^6$ vc/ml. The batch infection process took place in 10 L bioreactors at 35° C. at a multiplicity of infection of 1. At the time of harvest, 20-24 hours post-infection, a Domiphen Bromide (DB) stock solution was added in 30 minutes while stirring to reach a final DB concentration of 2.2 mM DB. After detergent addition, the bioreactor was left to incubate for one hour at 35° C., while constantly stirring.

Samples of the crude cell harvest (without DB treatment and post-DB treatment) were centrifuged (3000 g, 5 minutes) to sediment the cells. The crude samples (not centrifuged prior to DB treatment, thus containing the cells) and the supernatant samples were analyzed for poliovirus and host cell DNA quantification, using a D-antigen ELISA and Q-PCR, respectively.

Figure 3:
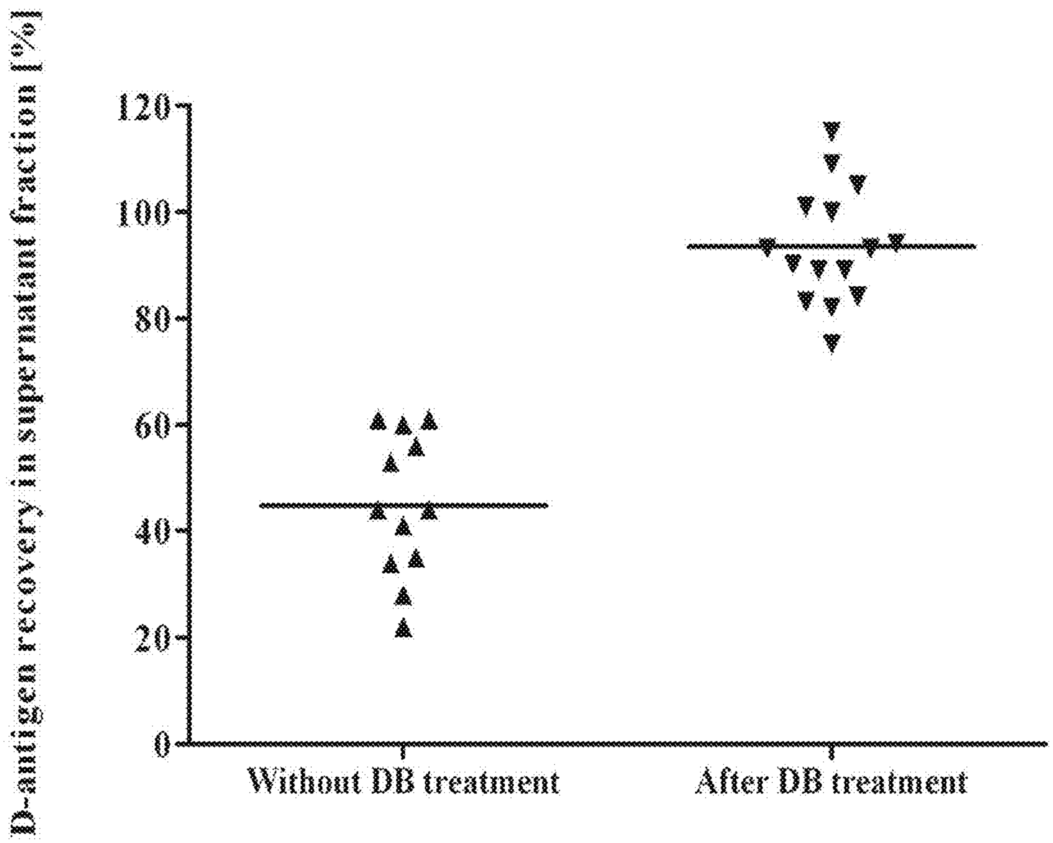
FIG. 3. Ratio D-antigen concentration in supernatant/D-antigen concentration in crude, before and after treatment with a detergent. Ratios were measured for several harvests with distinct cell densities and containing different polio strains (Mahoney, MEF-1 or Saukett).

The results depicted in FIG. 3 show that in all runs (for all three strains), the detergent treatment resulted in a two-fold increase of D-antigen release, from the crude poliovirus harvest into the liquid phase. In addition, DNA was effectively precipitated by the treatment with DB. In all runs, the DNA clearance in respect to crude harvest was more than 5 log after detergent treatment, as opposed to 2 log prior to detergent treatment (data not shown). This demonstrates that the disclosure can also be used at bioreactor scale.

The addition of a detergent had been used previously to remove host cell DNA in the field of adenovirus purification processes, as disclosed in, e.g., U.S. Pat. No. 7,326,555 and WO 2011/045378. However, selective DNA precipitation has not been disclosed hitherto in the field of poliovirus purification. Polioviruses and adenoviruses are very distinct viruses. Indeed, a poliovirus is composed of a single-stranded RNA genome encapsulated with a protein capsid and the viral particle is about 30 nanometers in diameter. In contrast, adenoviruses represent the largest non-enveloped viruses, with a diameter of about 90-100 nm. The protein capsid of the adenovirus contains a double-stranded DNA helix and is uniquely populated with fibers or spikes that aid in attachment to the host cell, which are absent in polioviruses. The isoelectric point of adenoviruses is around pH 5.5, which means that the virus is negatively charged under physiological conditions. A review article about the isoelectric point of poliovirus suggests that its value is higher than for adenoviruses pH 5.8-7.5 (Thomassen et al., 2013). As size and charge are key determinants in chromatography and precipitation processes, it could not have been predicted that the treatment with a detergent would have a similar effect on a poliovirus-containing crude cell culture harvest as it has on an adenovirus-containing crude cell culture harvest.

More importantly, the unexpected effect of detergent treatment on the release of poliovirus particles from the crude cell culture harvest into the liquid phase of the harvest had not been observed in the purification methods for adenoviruses. Thus, this surprising effect could not have been foreseen based on previously used virus purification methods.

Example 4

Poliovirus Purification Process with and without Detergent Treatment and Impact on D-antigen Recovery and DNA Clearance PER.C6® cells were grown in a serum-free culture medium in a 10 L bioreactor operated in perfusion mode to a cell density of approximately $50\times10^6$ vc/ml. Prior to infection with poliovirus serotype 1 (Mahoney) or type 3 (Saukett), the culture was diluted with fresh culture medium to a viable cell density of $11\times10^6$ vc/ml and $9.5\times10^6$ vc/ml, respectively. The batch infection process took place in 10 L bioreactors at 35° C. at a multiplicity of infection of 1. At the time of harvest, 22 hours post-infection, two 1.5 L bulk samples were taken from the bioreactor and transferred into 2 L bottles. One bottle was taken to perform direct filtration; the other was treated with a detergent (DB) and subsequently subjected to filtration.

DB treatment was performed in a 2 L bottle at room temperature. DB stock solution was added via a pipette in 30 equal portions in 30 minutes while stirring to reach a final DB concentration of 2.1 mM. After detergent addition, the bottle was left to incubate for two hours while mixing. Cell clarification was performed by passing the untreated crude harvest or DB-treated harvest through a series of filters, i.e., a positively charged depth filter (MILLIPORE® MILLISTAK+® HC POD DOHC) with a pore size distribution of 4-8/0.6-1.5 μm, followed by two consecutive polyether sulfon (PES) membrane filters of reducing size 0.8/0.45 μm (SARTORIUS®, SARTOPORE® 2) and 0.22 μm (MILLIPORE®, MILLIPAK®). During filtration, the first received filtrate was discarded, then filtrate was collected in a product bottle until the feed bottle was empty. Recovery of the virus was completed by addition of 1 system volume of PBS to the collected filtrate. The clarified harvest was analyzed for virus quantity, host cell DNA and HCP using a D-antigen ELISA, Q-PCR and host cell-specific protein ELISA, respectively. The impact of DB treatment on the performance of the harvest process is depicted in Table 2. Recovery is calculated with respect to a whole broth sample taken from the crude harvest at the time of harvest.

Consistent with the previous examples, the D-antigen recovery after treatment with a detergent (domiphen bromide) was significantly increased compared to the process without domiphen bromide. As a result, the volumetric productivity of the process was significantly increased. Indeed, the concentration of D-Antigen in the clarified harvest was doubled after detergent (DB) treatment.

Furthermore, clearance of HC-DNA by the detergent treatment step was observed, which was in accordance with the results described in previous examples. According to Table 2, the treatment of a crude cell harvest containing poliovirus with a detergent (DB) helped to clear DNA by a factor of 1000. Moreover, it shows that Host Cell Proteins (HCP) were partly removed by the use of detergent.

TABLE 2

Clarification of 1.5 L crude virus harvest with (+) and without (−) DB treatment for two virus strains

| | Strain | | | |
|---|---|---|---|---|
| | Mahoney | | Saukett | |
| | Viable cell density at infection | | | |
| | 11 | | 9.5 | |
| | DB treatment | | | |
| | − | + | − | + |
| Clarified harvest | | | | |
| D-antigen concentration (DU/ml) | 1439 | 2977 | 510 | 1195 |
| HC-DNA concentration (pg/ml) | 1731 | <0.4 | 702 | <0.4 |
| HCP concentration (μg/ml) | 79 | 52 | 76 | 55 |
| D-antigen harvest recovery (%) | 57 | 110 | 52 | 122 |
| DNA log removal | 1.9 | >5.5 | 2.1 | >5.3 |
| HCP removal (%) | 25 | 54 | 38 | 55 |

Example 5

DB Treatment as Part of Drug Substance Manufacturing Inactivated Poliovirus Vaccine (IPV) Process This example demonstrates the purification of wild-type poliovirus serotypes (Mahoney, MEF-1 and Saukett) from a crude cell culture harvest at 20 L scale. The downstream process steps involved are depicted in FIG. 3.

PER.C6® cells were grown in a serum-free culture medium in a 10 L bioreactor operated in perfusion mode to a cell density of approximately $50\times10^6$ vc/ml. Prior to infection with poliovirus serotype 1 (Mahoney), type 2 (MEF-1) or type 3 (Saukett), the culture was divided over three bioreactors and diluted with fresh culture medium to a viable cell density of $12\times10^6$ vc/ml, $11\times10^6$ vc/ml and $13\times10^6$ vc/ml, respectively. The batch infection process took place in 10 L bioreactors at 35° C. at a multiplicity of infection of 1.

At the time of harvest, 23 hours post-infection, DB stock solution was added to the bioreactors over a period of 30 minutes, to a final DB concentration of 2.2 mM DB. After detergent addition, the DB-treated harvest was mixed for 60 minutes. Subsequently, clarification was performed by passing the DB-treated harvest through a series of filters, i.e., two 8-4/1.5-0.6 μm MILLISTAK® DOHC POD filters in parallel, followed by a 0.8/0.45 μm SARTOPORE® 2 filter, a Single Sep Q filter and, finally, a 0.22 μm MILLIPAK® filter.

The clarified harvest of two filtrations was pooled, acidified to pH 5.0 and diluted to conductivity 11 mS/cm and filtered over a SARTORIUS® SARTOPORE® 0.8/0.45 μm filter prior to loading to a SARTORIUS® SARTOBIND® S membrane. The virus was retrieved from the membrane by step elution using PBS. In the final step, the cation exchange (CEX) virus fraction was loaded on a column packed with SEPHAROSE® 6FF size exclusion chromatography resin with fractionation range 10-4000 kDa. During isocratic elution, residual HCPs were separated from the virus fraction pool, and also the matrix of the poliovirus was fully exchanged to a phosphate buffer containing NaCl.

Following purification, the purified virus solution was further diluted with SEC elution buffer to a preset absorbance unit (OD 260 nm), then M199 and glycine (final concentration 5 g/L) were added and the fluid was filtered over a 0.22 μm pore size filter prior to formaldehyde inactivation.

Inactivation was performed using 0.025% formalin during 13 days (with in between 0.22 μm filtration) at 37° C. according to the World Health Organisation (WHO) and European Pharmacopeia (EP) requirements.

In the above-described process, the main product intermediates, crude harvest, clarified harvest, SEC eluate and inactivated polio virus (IPV) were analyzed for virus quantity, host cell DNA and total protein (TP) using a D-antigen ELISA, Q-PCR and Bradford assay, respectively.

Results and Discussion

Figure 5:
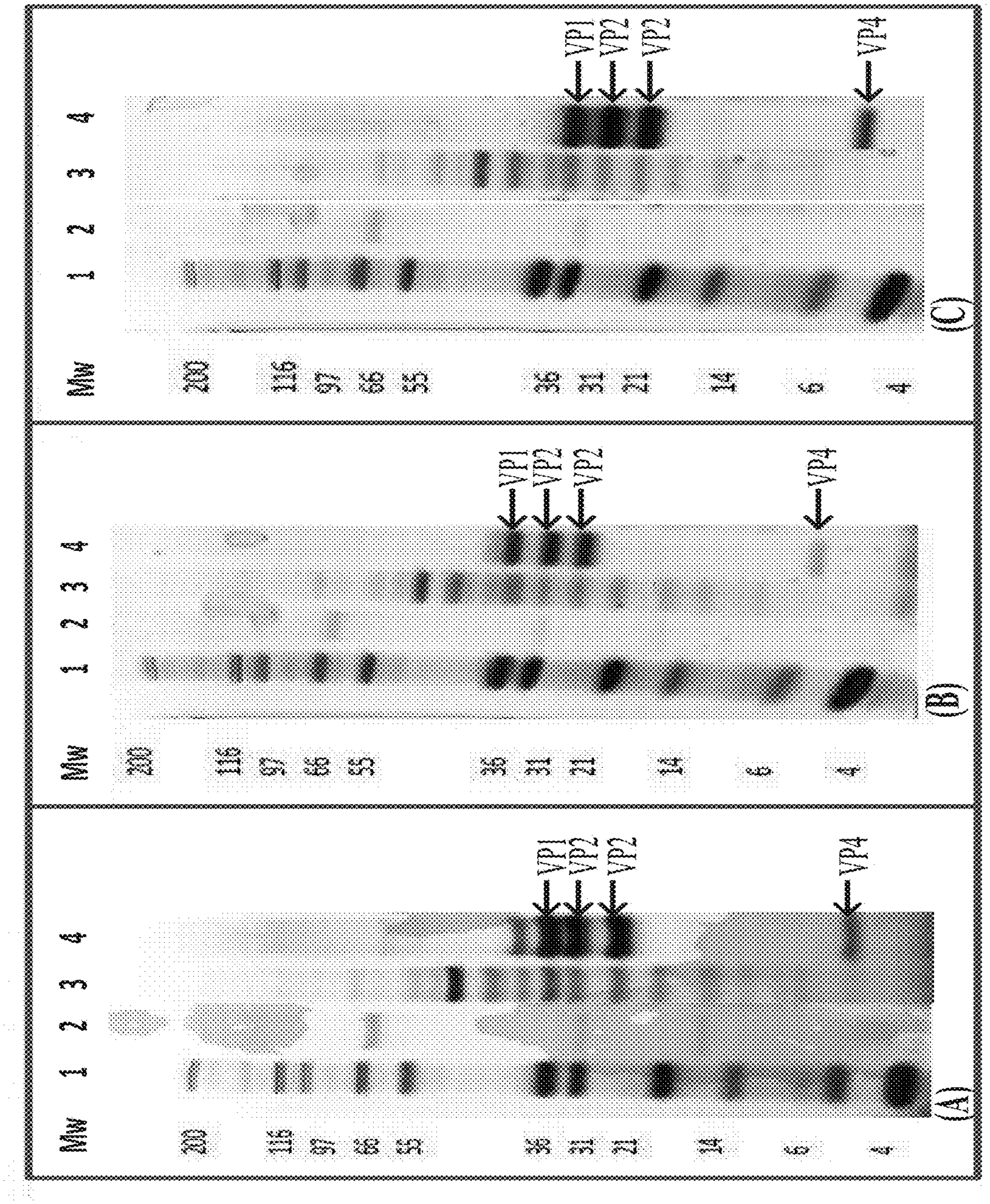
FIG. 5. Product characterization by SDS-PAGE of poliovirus strains (Panel A) Mahoney, (Panel B) MEF-1, (Panel C) Saukett. 1=Marker, 2=System suitability control, 3=CEX eluate, 4=SEC eluate.

Table 3 summarizes the quality attributes and yields of purified poliovirus per serotype. Residual specific protein and DNA concentration meet regulatory requirements (WHO/EP). In addition, the absorbance ratio OD260/OD280 is indicative for highly purified virus (Westdijk et al., 2011). Finally, SDS-PAGE gels of the different serotypes show four major protein bands corresponding to the surface proteins of the poliovirus (FIG. 5). Hence, the purification process described herein is robust for the purification of all three serotypes, irrespective of differences in the surface properties of the serotypes and the virus titers at harvest.

TABLE 3

Quality of monovalent Inactivated Polio Virus and purified poliovirus (SEC eluate) for the monovalent Inactivated Polio Virus manufacturing process

| | monovalent Inactivated Polio Virus | | | SEC eluate | |
|---|---|---|---|---|---|
| Serotypes | D-Antigen (DU/mL) | TP/DU (μg/DU) | HC-DNA (pg/DU) | OD260/OD280 (—) | Purity on SDS page gel |
| Mahoney | 2014 | 0.008 | <0.2 | 1.67 | VP1, VP2, VP3 and |
| MEF-1 | 343 | 0.037 | <1.2 | 1.75 | VP4 are the major |
| Saukett | 1201 | 0.012 | <0.3 | 1.71 | bands (see FIG. 5) |

Process performance is evaluated based on clearance of host cell impurities, DNA and HCP as well as step yields for the different production stages. Results are depicted in Table 4.

TABLE 4

Process performance of the monovalent Inactivated Polio Virus Manufacturing process

| | Process stage | | | | | | | | |
|---|---|---|---|---|---|---|---|---|---|
| | D-antigen recovery [%] | | | HCP removal [%] | | | DNA log removal | | |
| | Type 1 | Type 2 | Type 3 | Type 1 | Type 2 | Type 3 | Type 1 | Type 2 | Type 3 |
| Harvest | 86 | 77 | 101 | 40 | 51 | 42 | >5.6 | >5.6 | >5.5 |
| Purification | 42 | 39 | 56 | >99.9 | >99.9 | >99.9 | * | * | * |
| Inactivation | 89 | 77 | 82 | NA | NA | NA | NA | NA | NA |
| Overall | 32 | 23 | 46 | >99.9 | >99.9 | >99.9 | >5.6 | >5.6 | >5.5 |

* Removal could not be determined as feed was already below detection level

For all three serotypes, residual HC-DNA levels after the clarification step are below the limit of quantification. Table 5 shows overall productivity of poliovirus expressed in equivalent dose/ml cell culture. This calculation is based on a 40:8:32 ratio D-antigen Units/dose for poliovirus types 1-3. Comparison of the final productivity after inactivation shows that this process exceeds the current worldwide IPV manufacturing VERO cell process platform, which yields 0.64, 1.04 and 0.34 dose/ml virus culture for types 1-3, respectively (Kreeftenberg, 2007). Hence, it can be concluded that despite the high initial impurity level in the feed originating from the high cell density harvest, a high resolution and high recovery process was developed, yielding unsurpassed high productivities for monovalent inactivated polio virus bulk production as an integral part of IPV vaccine manufacturing.

TABLE 5

Productivity of the 20 L monovalent Inactivated Polio Virus Manufacturing process (# equivalent doses/ml cell culture)

| Product intermediate | Type 1 (Mahoney) | Type 2 (MEF-1) | Type 3 (Saukett) |
|---|---|---|---|
| Crude harvest | 69 | 37 | 29 |
| Clarified harvest | 53 | 32 | 29 |

TABLE 5-continued

| Productivity of the 20 L monovalent Inactivated Polio Virus Manufacturing process (# equivalent doses/ml cell culture) | | | |
|---|---|---|---|
| Product intermediate | Type 1 (Mahoney) | Type 2 (MEF-1) | Type 3 (Saukett) |
| Purified harvest | 22 | 12 | 16 |
| Inactivated polio virus bulk | 20 | 9.4 | 13 |

Example 6

Increased Poliovirus Purification Yields from Crude Cell Culture Harvest by Addition of Different Cationic Detergents PER.C6® cells were grown in a serum-free culture medium in a 10 L bioreactor operated in perfusion mode to a cell density of approximately $50\times10^6$ vc/ml. Prior to infection with poliovirus type 2 (MEF-1), the culture was diluted with fresh culture medium to a viable cell density of about $12.5\times10^6$ vc/mL. The batch infection process took place in 10 L bioreactors at 35° C., at a multiplicity of infection of 1. At the time of harvest, 20-24 hours post-infection, a 120 ml sample was taken, which was subsequently distributed in 18 aliquots of 5 mL.

In order to determine the effect of a detergent on the poliovirus containing crude cell harvests, a titration experiment was performed with several cationic detergents; Hexadecyltrimethylammonium bromide (CTAB), Hexadecylpyridinium chloride (CPC) and Benzethonium chloride (BTC). A fixed amount of CTAB, CPC and BTC stock solutions (69, 70, 56 mM, respectively, all including 40 mM NaCl) were added to the harvest aliquots at a targeted detergent concentration (between 0 and 4 mM). The samples were thoroughly mixed and incubated for one hour at 35° C. Subsequently, the samples were centrifuged for 5 minutes at 3000 g to spin down precipitated DNA. Supernatant samples were analyzed for virus quantity by D-antigen ELISA and for host cell DNA using Q-PCR.

Figure 6:
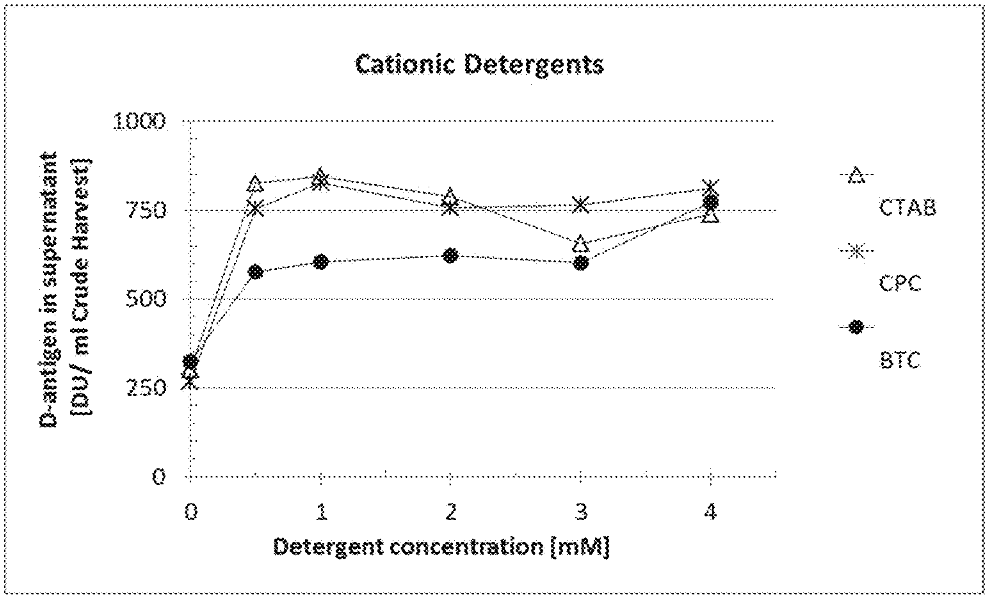
FIG. 6. (Panel A) D-antigen release from poliovirus-containing crude cell culture harvests as a result of the treatment with different cationic detergents; CTAB, CPC and BTC, respectively.
Figure 6:
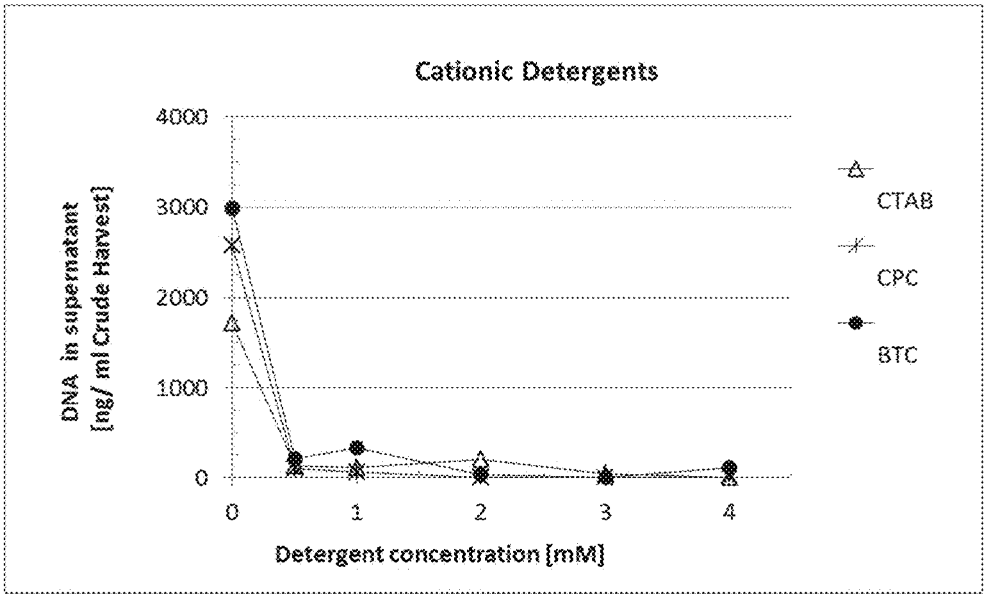

FIG. 6 (Panel A) shows D-antigen release from poliovirus-containing crude cell culture harvests as a result of the treatment with different cationic detergents; CTAB, CPC and BTC, respectively. The D-antigen concentrations in the supernatant, which are corrected for the detergent addition dilution, are disclosed as a function of the detergent concentration. FIG. 6 (Panel A) discloses that after the addition of a detergent (CTAB, CPC and BTC), the virus titer increased substantially as compared to before the addition of a detergent (CTAB, CPC and BTC). For each cationic detergent, the same pattern can be observed, i.e., increasing the detergent (CTAB, CPC and BTC) concentration leads to increased virus release from the crude cell harvest into the liquid phase.

FIG. 6 (Panel B) shows host cell DNA precipitation in poliovirus-containing crude cell culture harvests as a result of the treatment with a detergent (CTAB, CPC and BTC). The concentrations on the y-axis have been corrected for the detergent dilution factor. For each cationic detergent, the same pattern can be observed, i.e., host cell DNA is precipitated from the crude cell culture harvest. FIG. 6 (Panel B) clearly indicates that effective DNA clearance occurred in the aliquots for detergent (CTAB, CPC or BTC) concentrations above 0.5 mM.

Since the increase of detergent did not lead to poliovirus precipitation, a person skilled in the art would extrapolate these results to poliovirus-containing cell suspensions of even higher cell densities, e.g., of about $70\times10^6$ cells/mL, e.g., of about $90\times10^6$ cells/mL, e.g., up to about $120\times10^6$ cells/mL, e.g., up to about $150\times10^6$ cells/mL. The skilled person would conclude that the poliovirus from such high cell density crude cell culture harvests can be purified by the methods of this disclosure.

Example 7

Increased Poliovirus Purification Yields from Crude Cell Culture Harvest by Addition of Different Types of Detergents (Anionic, Zwitterionic and Non-ionic)

PER.C6® cells were grown in a serum-free culture medium in a 10 L bioreactor operated in perfusion mode to a cell density of approximately $50\times10^6$ vc/ml. Prior to infection with poliovirus, type 2 (MEF-1), the culture was diluted with fresh culture medium to a viable cell density of about $12.5\times10^6$ vc/mL. The batch infection process took place in 10 L bioreactors at 35° C., at a multiplicity of infection of 1. At the time of harvest, 20-24 hours post-infection, a 240 ml sample was taken, which was subsequently distributed in 42 aliquots of 5 mL.

In order to determine the effect of a detergent on the poliovirus-containing crude cell harvests, a titration experiment was performed with several different types of detergents. Anionic detergents (Sodium taurodeoxycholate hydrate (STH) and Sodium dodecyl sulfate (SDS)), Zwitterionic detergents (3-(N,N-Dimethylmyristyl ammonio)propanesulfonate (SB3-14), and 3-[(3-Cholamidopropyl)dimethyl ammonio]-1-propanesulfonate (CHAPS)), and Non-ionic detergents (4-(1,1,3,3-Tetramethylbutyl)phenyl-polyethylene glycol (TRITON® X-100) and Decyl-β-D-1-thiomaltopyranoside (DTP)) were used as exemplary detergents for their detergent class. A fixed amount of detergent stock solutions were added to the harvest aliquots at a targeted detergent concentration. The targeted detergent concentration for anionic detergents (STH and SDS), zwitterionic detergents (SB3-14 and CHAPS), and for non-ionic detergents (TRITON® X-100 and DTP) was between 0 and 4 mM. The samples of all detergent types (anionic, zwitterionic, non-ionic) were thoroughly mixed and incubated for one hour at 35° C. Subsequently, the samples were centrifuged for 5 minutes at 3000 g to spin down precipitated DNA. Supernatant samples were analyzed for virus quantity by D-antigen ELISA and for host cell DNA using Q-PCR.

Figure 7:
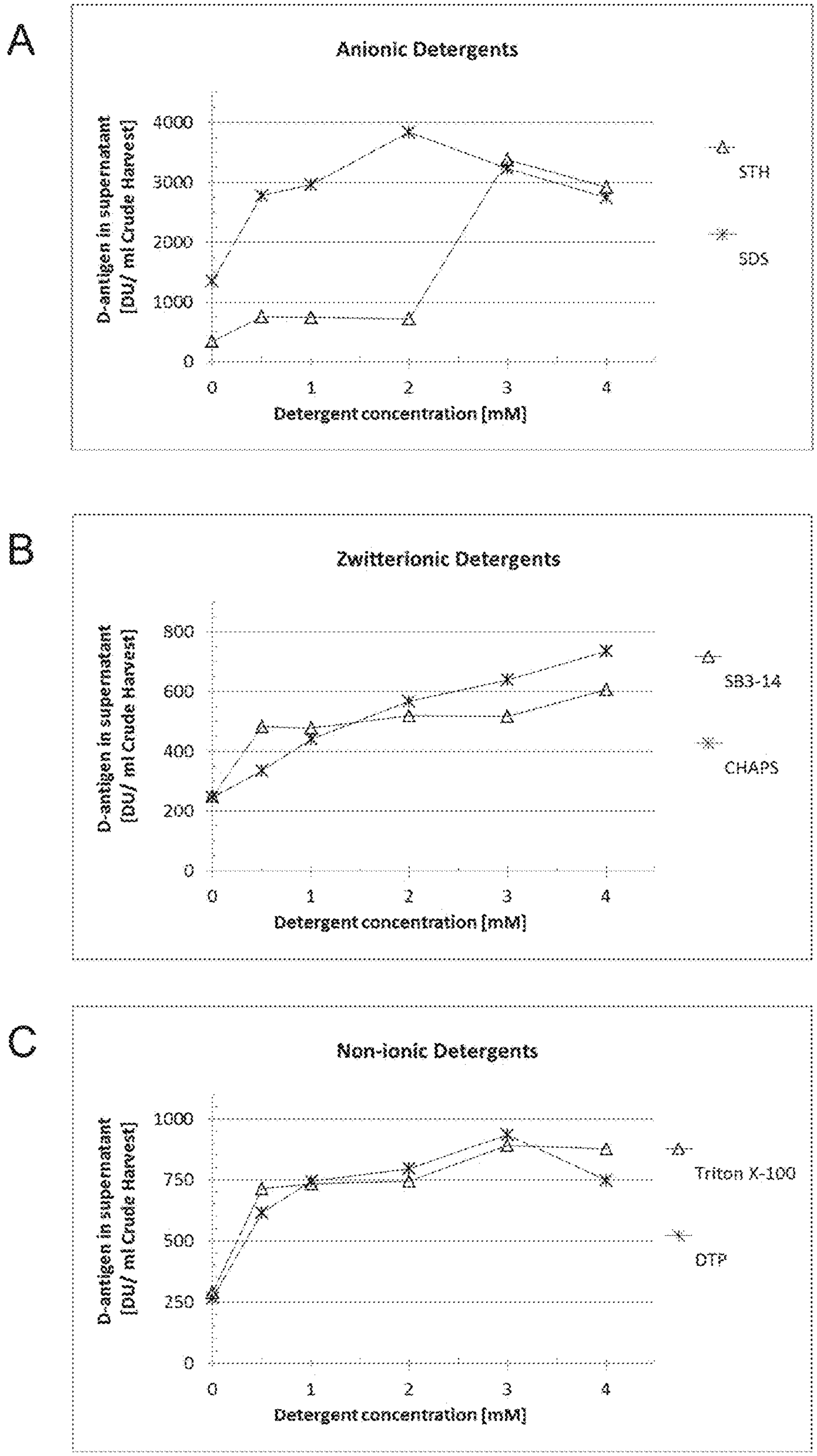
FIG. 7 (Panels A, B and C). D-antigen release from poliovirus-containing crude cell culture harvests as a result of the treatment with different types of detergents (Anionic, zwitterionic and non-ionic detergents).
Figure 8:
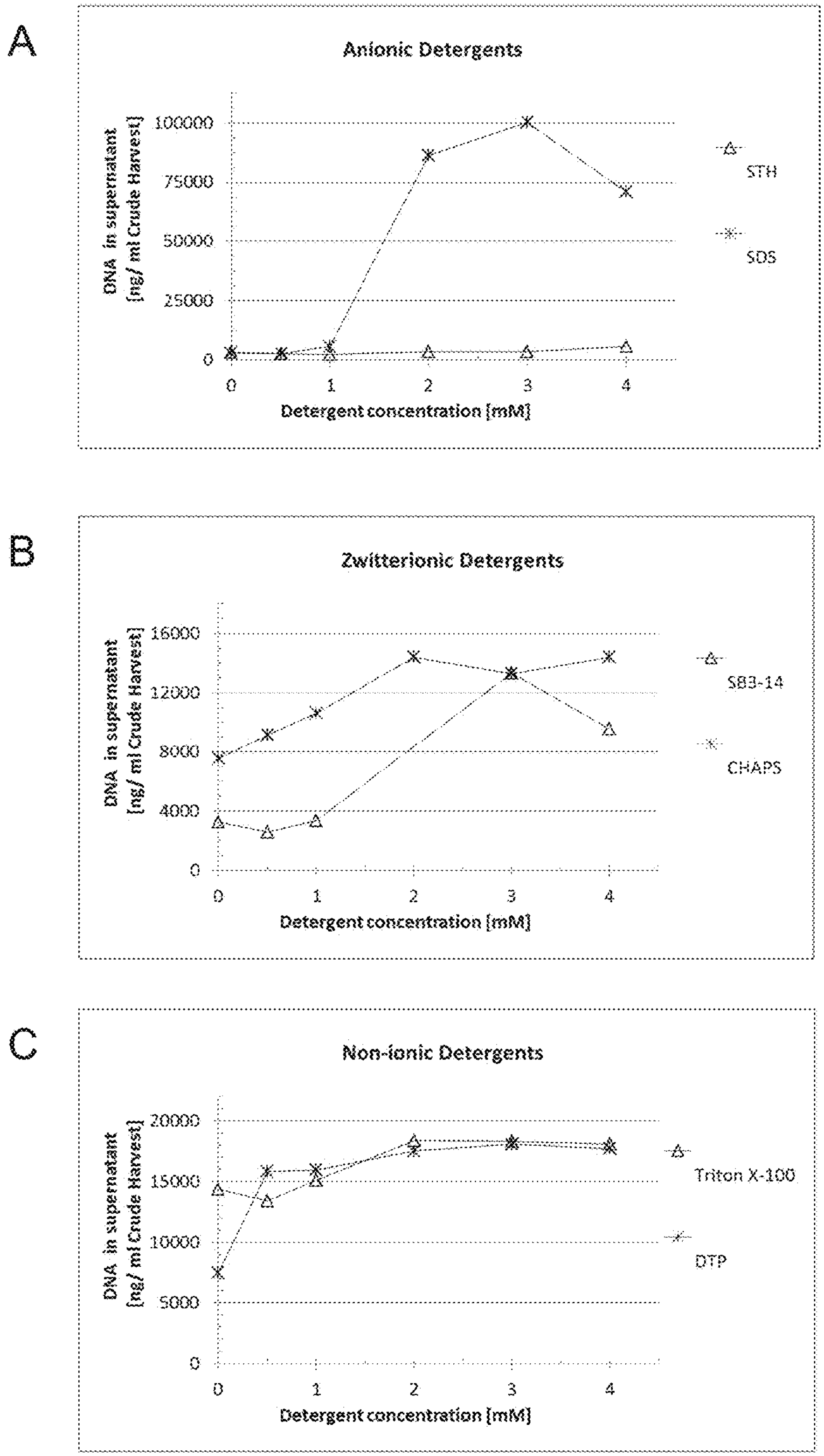
FIG. 8 (Panels A, B and C). Host cell DNA precipitation in poliovirus-containing crude cell culture harvests as a result of the treatment with different types of detergents (Anionic, zwitterionic and non-ionic detergents).

FIG. 7 (Panels A, B, and C) shows D-antigen release from poliovirus-containing crude cell culture harvests as a result of the treatment with different types of detergents, anionic detergents (STH and SDS), zwitterionic detergents (SB3-14 and CHAPS) and non-ionic detergents (TRITON® X-100 and DTP), respectively. The D-antigen concentrations in the supernatant, which are corrected for the detergent addition dilution, are disclosed as a function of the detergent concentration. FIG. 7 (Panels A, B and C) discloses that after the addition of a detergent (STH, SDS, SB3-14, CHAPS, TRITON® X-100 and DTP), the virus titer increased substantially as compared to before the addition of a detergent (STH, SDS, SB3-14, CHAPS, TRITON® X-100 and DTP). For each type of detergent (anionic, zwitterionic or non-ionic), the same pattern can be observed, i.e., increasing the detergent (STH, SDS, SB3-14, CHAPS, TRITON® X-100 and DTP) concentration leads to increased virus release from the crude cell harvest into the liquid phase. FIG. 8 (Panels A, B and C) shows host cell DNA release from poliovirus-containing crude cell culture harvests as a result of the treatment with a detergent (STH, SDS, SB3-14, CHAPS, TRITON® X-100 and DTP). The concentrations on the y-axis have been corrected for the detergent dilution factor. For each type of detergent (anionic, zwitterionic or non-ionic), the same pattern can be observed, i.e., increasing the detergent (STH, SDS, SB3-14, CHAPS, TRITON® X-100 and DTP) concentration leads to increased host cell DNA release from the crude cell harvest into the liquid phase.

Since increase of concentration of the detergent types (anionic, zwitterionic or non-ionic) did not lead to poliovirus precipitation, a person skilled in the art can extrapolate these results to poliovirus-containing cell suspensions of even higher cell densities, e.g., of about $70\times10^6$ cells/mL, e.g., of about $90\times10^6$ cells/mL, e.g., up to about $120\times10^6$ cells/mL, e.g., up to about $150\times10^6$ cells/mL. The skilled person would conclude that the poliovirus from such high cell density crude cell culture harvests can be purified by the methods of this disclosure.

Example 8

DB Treatment and Clarification as Part of the Sabin IPV Purification Train

This example describes the application of the harvest process (DB treatment followed by cell clarification) as part of the purification process of attenuated poliovirus serotypes (Sabin type 1, Sabin type 2 and Sabin type 3) from crude cell culture harvests.

Cells, from the PER.C6® cell line, cells were grown in a serum-free culture medium in a 10 L bioreactor operated in perfusion mode to a cell density of approximately $50\times10^6$ vc/ml. Prior to infection with poliovirus serotype 1 (Sabin type 1), type 2 (Sabin type 2) or type 3 (Sabin type 3), the culture was diluted with fresh culture medium to a viable cell density of $12.5\times10^6$ vc/ml or $25\times10^6$ vc/ml. Multiplicity of infection of 1 and 0.1 were used for the $12.5\times10^6$ vc/ml and $25\times10^6$ vc/ml cell cultures, respectively. In both cases, the batch infection process took place in 10 L bioreactors at 32.5° C.

Figure 4:
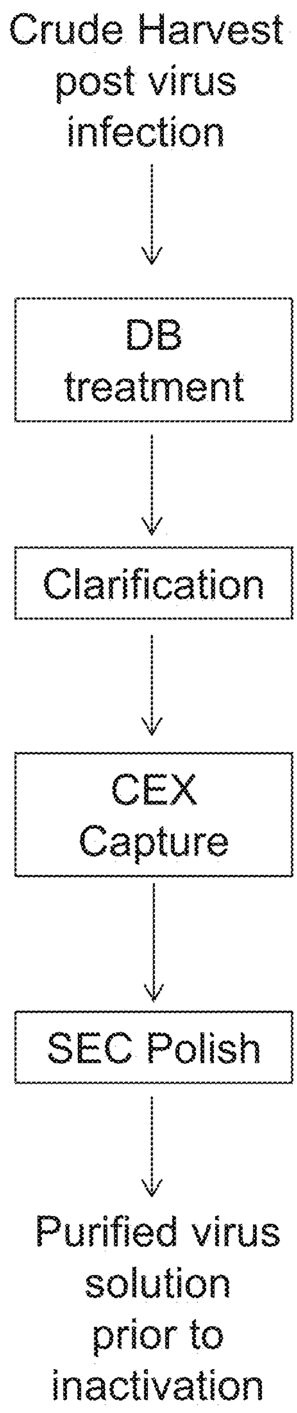
FIG. 4. Poliovirus purification flow chart.

At the time of harvest (48 hours post-infection for Sabin type 1 or Sabin type 3, and 72 hours post-infection for Sabin type 2), DB stock solution was added to the bioreactors over a period of 30 minutes, to a final DB concentration of 2.2 mM DB. After detergent addition, the DB-treated harvest (~11 L) was mixed for 60 minutes. Finally, the DB-treated harvest was clarified and purified similarly as described for Salk IPV in FIG. 4 and Example 5.

Table 6 shows the overall D-Antigen recovery and HC-DNA removal of the DB treatment step followed by serial filtration. Table 7 summarizes the quality attributes of purified Sabin poliovirus.

TABLE 6

D-antigen recovery and HC-DNA concentration after DB treatment and cell clarification step.

| Serotypes | VCDAI ($\times10^6$ vc/ml) | D-antigen recovery (%) | HC-DNA (ng/ml) |
|---|---|---|---|
| Sabin type 2 | 12.5 | 126 | <0.4 |
| Sabin type 3 | 12.5 | 105 | <0.4 |
| Sabin type 1 | 25 | 83 | <0.4 |
| Sabin type 2 | 25 | 76 | <0.4 |
| Sabin type 3 | 25 | 85 | <0.4 |

TABLE 7

Quality of purified Sabin polio virus before inactivation

| Serotypes | VCDAI ($\times10^6$ vc/ml) | TP/DU (μg/DU) | HC-DNA (pg/DU) | OD260/OD280 (—) |
|---|---|---|---|---|
| Sabin type 2 | 12.5 | 0.040 | <1.3 | 1.72 |
| Sabin type 3 | 12.5 | 0.004 | <0.2 | 1.63 |
| Sabin type 1 | 25 | 0.009 | <0.3 | 1.74 |
| Sabin type 2 | 25 | 0.03 | <1.1 | 1.67 |
| Sabin type 3 | 25 | —* | <0.3 | 1.84 |

*Not available due to one or more missing data.

The results for the Sabin polio virus process show large similarity with the results achieved for the wild-type strains. Also, for Sabin polio virus strains, the combined DB treatment and clarification harvest process achieves high virus recovery with complete removal of HC-DNA (Table 6). Table 7 shows that the PER.C6®-based Sabin polio virus cell culture harvests could be sufficiently purified using the harvest and purification process described in the disclosure. Residual specific protein and DNA concentration meet regulatory requirements (WHO/EP). In addition, the absorbance ratio OD260/0D280 is indicative for highly purified virus (Westdijk et al., 2011). Overall purity is the same as purity obtained for wild-type polio virus strains (see Table 3 in Example 5).

The results are very promising, especially when one considers that the two types of viruses, wild-type and Sabin strains, differ in net surface charge (Thomassen et al., 2013). This once more demonstrates the robustness of the developed generic high productivity polio virus vaccine manufacturing process.

REFERENCES

Bakker W. A. M., Y. E. Thomassen, A. G. van't Oever, J. Westdijk, M. G. C. T. van Oijen, L. C. Sundermann, P. van't Veld, E. Sleeman, F. W. van Nimwegen, A. Hamidi, G. F. A. Kersten, N. van den Heuvel, J. T. Hendriks, and L. A. van der Pol. Inactivated polio vaccine development for technology transfer using attenuated Sabin poliovirus strains to shift from Salk-IPV to Sabin-IPV. *Vaccine* 2011; 29(41):7188-96.

Cortin V., J. Thibault, D. Jacob, and A. Gamier. High-Titer Poliovirus Vector Production in 293 S Cell Perfusion Culture. *Biotechnol. Prog.* 2004.

European Pharmacopoeia 7.0, Poliomyelitis vaccine (inactivated). 04/2010:0214.

Fuchs F., P. Minor, A. Daas, and C. Milne. Establishment of European Pharmacopoeia BRP batch 2 for inactivated poliomyelitis vaccine for in vitro D-antigen assay. *Pharmeuropa Bio.* 2003-1, 23-50, 2003.

Goerke A., B. To, A. Lee, S. Sagar, and K. Konz. Development of a Novel Poliovirus Purification Process Utilizing Selective Precipitation of Cellular DNA. *Biotechnology and Bioengineering,* Vol. 91, No. 1, Jul. 5, 2005.

Henderson M., C. Wallis, and J. Melnick. Concentration and purification of enteroviruses by membrane chromatography. *Applied and Environmental Microbiology,* November 1976, p. 689-693.

Kreeftenberg H., T. van der Velden, G. Kersten, N. van der Heuvel, and M. de Bruijn. Technology transfer of Sabin-IPV to new developing country markets. *Biologicals* 2006; 34(2): 155-8.

Sanders B. A., D. Edo-Matas, J. H. H. V. Custers, M. H. Koldijk, V. Klaren, M. Turk, A. Luitjens, W. A. M. Bakker, F. UytdeHaag, J. Goudsmit, J. A. Lewis, and H. Schuitemaker, PER.C6® cells as a serum-free suspension cell platform for the production of high titer poliovirus: a potential low cost of goods option for world supply of inactivated poliovirus vaccine. *Vaccine* 2013; 31(5):850-6.

Thomassen Y. E., A. G. van't Oever, M. Vinke, A. Spiekstra, R. H. Wijffels, L. A. van der Pol, and W. A. M. Bakker. Scale down of the inactivated polio production process. *Biotechnology and Bioengineering,* Vol. 110 (5): 1354-1365, May 2013.

Thomassen Y. E., G. van Eikenhorst, L.A. van der Pol, and W. A. M. Bakker. Isoelectric focusing with whole column imaging detection. *Anal. Chem.* 85:6089-6094 (2013).

D. H. W. Vlecken, R. P. M. Pelgrim, S. Ruminsk, W. A. M. Bakker, and L. A. van der Pol. Comparison of initial feasibility of host cell lines for viral vaccine production. *Journal of Virological Methods* 2013 193 (2):278-283.

Westdijk J., D. Brugmans, J. Martin, A. van't Oever, W. A. M. Bakker, L. Levels, and G. Kersten. Characterization and standardization of Sabin-based inactivated polio vaccine: Proposal for a new antigen unit for inactivated polio vaccines. *Vaccine* 2011; 29:3390-3397.

WHO technical report Series, No. 910, 2002. Recommendations for the production and control of poliomyelitis vaccine (inactivated).

Yuk I. H. Y., M. M. Olsen, S. Geyer, and S. P. Forestell. Perfusion Cultures of Human Tumor Cells: A Scalable Production Platform for Oncolytic Adenoviral Vectors. *Biotechnol. Bioengin.* 86:637-641 (2004).

The invention claimed is:

1. A method of purifying poliovirus from a crude cell culture harvest containing poliovirus, said method comprising the steps of:

a) adding a cationic detergent to the crude cell culture harvest to obtain a mixture; and b) clarifying a mixture obtained from step a) to obtain a clarified harvest with poliovirus particles;

wherein the combination of step a) and step b) results in a reduction in host cell DNA of at least 4 log 10.

2. A method of enhancing poliovirus release from a crude cell culture harvest containing poliovirus, said method comprising the steps of:

a) adding a cationic detergent to the crude cell culture harvest to obtain a mixture; and b) clarifying a mixture obtained from step a) to obtain a clarified harvest with poliovirus particles;

wherein the combination of step a) and step b) results in a reduction in host cell DNA of at least 4 log 10.

3. A method of purifying poliovirus from a crude cell culture harvest containing poliovirus, said method comprising the steps of:

a) adding a cationic detergent to the crude cell culture harvest to obtain a mixture;

b) clarifying a mixture obtained from step a) to obtain a clarified harvest with poliovirus particles; and c) subjecting the clarified harvest obtained in step b) to a capture step to obtain a poliovirus-containing suspension;

wherein the combination of step a) and step b) results in a reduction in host cell DNA of at least 4 log 10.

4. The method of purifying poliovirus from a crude cell culture harvest according to claim 3, wherein said capture step is a cationic exchange chromatography step.

5. The method according to claim 3, wherein the poliovirus obtained in step c) is further separated from the poliovirus-containing suspension by size exclusion.

6. The method according to claim 5, wherein said size exclusion is performed by size exclusion chromatography.

7. A method of purifying poliovirus from a crude cell culture harvest containing poliovirus, said method comprising the steps of:

a) adding a cationic detergent to the crude cell culture harvest to obtain a mixture;

b) clarifying a mixture obtained from step a) to obtain a clarified harvest with poliovirus particles;

c) subjecting the clarified harvest obtained in step b) to a cationic exchange chromatography step to obtain a poliovirus-containing suspension; and d) further separating the poliovirus from the poliovirus-containing suspension by size exclusion chromatography;

wherein the combination of step a) and step b) results in a reduction in host cell DNA of at least 4 log 10.

8. The method according to claim 1, wherein said cationic detergent is selected from the group consisting of Hexadecyltrimethylammonium bromide (CTAB), Hexadecylpyridinium chloride (CPC), Benzethonium chloride (BTC) and domiphen bromide (DB).

9. The method according to claim 8, wherein the cationic detergent is domiphen bromide (DB).

10. The method according to claim 4, wherein the poliovirus obtained in step c) is further separated from the poliovirus-containing suspension by size exclusion.

11. The method according to claim 10, wherein the size exclusion is performed by size exclusion chromatography.

* * * * *